United States Patent
Weber

(10) Patent No.: US 10,604,792 B2
(45) Date of Patent: Mar. 31, 2020

(54) METHOD AND ANALYSIS SYSTEM FOR TESTING A SAMPLE

(71) Applicant: Boehringer Ingelheim Vetmedica GmbH, Ingelheim am Rhein (DE)

(72) Inventor: Christoph Weber, Cologne (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 0 days.

(21) Appl. No.: 15/725,317

(22) Filed: Oct. 5, 2017

(65) Prior Publication Data

US 2018/0100187 A1    Apr. 12, 2018

(30) Foreign Application Priority Data

Oct. 7, 2016 (EP) .................................. 16020370

(51) Int. Cl.
  *C12Q 1/6825* (2018.01)
  *B01L 3/00* (2006.01)
  (Continued)

(52) U.S. Cl.
  CPC ...... *C12Q 1/6825* (2013.01); *B01L 3/502738* (2013.01); *B01L 3/502761* (2013.01); *B01L 7/52* (2013.01); *C12Q 1/686* (2013.01); *C12Q 1/6806* (2013.01); *C12Q 1/6837* (2013.01); *G01N 35/00029* (2013.01); *B01L 2200/0605* (2013.01); *B01L 2200/10* (2013.01); *B01L 2300/0636* (2013.01); *B01L 2300/0645* (2013.01); *B01L 2300/0663* (2013.01); *B01L 2300/087* (2013.01); *B01L 2300/0816* (2013.01); *B01L 2300/0864* (2013.01); *B01L 2300/1822* (2013.01); *B01L 2400/0487* (2013.01); *G01N 2035/00564* (2013.01)

(58) Field of Classification Search
  CPC .............. C12Q 1/6825; G01N 35/0029; B01L 3/502761
  See application file for complete search history.

(56) References Cited

U.S. PATENT DOCUMENTS 5,096,669 A    3/1992  Lauks et al.
7,914,655 B2   3/2011  Frey et al.
(Continued)

FOREIGN PATENT DOCUMENTS

EP    1 947 197 A1    7/2008
GB    2 436 616 A    10/2007
(Continued)

OTHER PUBLICATIONS

Christos Kokkinos, Anastasios Economou, Mamas I. Prodromidis; Electrochemical Immunosensors: Critical Survey of Different Architectures and Transduction Stragegies, Trends in Analytical Chemistry, BD. 79, May 1, 2016 (May 1, 2016), pp. 88-105, XP055355665, Amsterdam, NL.

(Continued)

*Primary Examiner* — Narayan K Bhat
(74) *Attorney, Agent, or Firm* — David S. Safran; Roberts Calderon Safran & Cole, P.C.

(57) ABSTRACT

A method and an analysis system for testing a biological sample, nucleic-acid products being hybridized to capture molecules of a sensor apparatus at different temperatures.

22 Claims, 5 Drawing Sheets

(51) Int. Cl.
  *B01L 7/00* (2006.01)
  *G01N 35/00* (2006.01)
  *C12Q 1/686* (2018.01)
  *C12Q 1/6806* (2018.01)
  *C12Q 1/6837* (2018.01)

(56) References Cited

U.S. PATENT DOCUMENTS

| | | | |
|---|---|---|---|
| 8,597,574 B2 | 12/2013 | Gumbrecht et al. | |
| 8,741,815 B2 | 6/2014 | Gordon et al. | |
| 9,110,044 B2 | 8/2015 | Gumbrecht et al. | |
| 9,651,568 B2 | 5/2017 | Putnam et al. | |
| 9,797,894 B2 | 10/2017 | Kumar et al. | |
| 2003/0064507 A1 | 4/2003 | Gallagher et al. | |
| 2005/0196756 A1* | 9/2005 | Schmidt | C12Q 1/6813 435/6.16 |
| 2007/0148678 A1 | 6/2007 | Ehben et al. | |
| 2009/0057147 A1 | 3/2009 | Kayyem | |
| 2009/0325276 A1* | 12/2009 | Battrell | B01F 11/0071 435/287.2 |
| 2012/0282602 A1 | 11/2012 | Drader et al. | |
| 2013/0067525 A1 | 3/2013 | Wang | |
| 2013/0203057 A1* | 8/2013 | Lemieux | C12Q 1/6823 435/6.11 |
| 2013/0316340 A1 | 11/2013 | Kelley et al. | |
| 2015/0141272 A1 | 5/2015 | Gordon | |
| 2015/0292005 A1 | 10/2015 | Tomita et al. | |
| 2016/0298178 A1 | 10/2016 | Lammertyn et al. | |

FOREIGN PATENT DOCUMENTS

| | | | |
|---|---|---|---|
| WO | 2015054546 A1 | 4/2015 | |
| WO | WO 2015/071338 | * | 5/2015 |

OTHER PUBLICATIONS

Harper et al.: "Selective Immobilization of DNA and Antibody Probes on Electrode Arrays: Simultaneous Electrochemical Detection of DNA and Protein on a Single Platform", 2007, Langmuir, vol. 23, pp. 8285-8287 (2007).

Harper et al.: "Selective Immobilization of DNA and Antibody Probes on Electrode Arrays: Simultaneous Electrochemical Detection of DNA and Protein on a Single Platform", 2007, Langmuir, vol. 23, pp. 8285-8287—Supplemental Information, pp. 1-5, (2007).

* cited by examiner

METHOD AND ANALYSIS SYSTEM FOR TESTING A SAMPLE

BACKGROUND OF THE INVENTION

Field of the Invention

The present invention relates to a method for testing a biological sample wherein amplification products are formed from analytes of the sample, and wherein the amplification products are bonded to corresponding capture molecules of a sensor apparatus. The invention is also directed to an analysis system for performing the testing method.

Preferably, the present invention deals with analyzing and testing a sample, in particular from a human or animal, particularly preferably for analytics and diagnostics, for example with regard to the presence of diseases and/or pathogens and/or for determining blood counts, antibodies, hormones, steroids or the like. Therefore, the present invention is in particular within the field of bioanalytics. A food sample, environmental sample or another sample may optionally also be tested, in particular for environmental analytics or food safety and/or for detecting other substances.

In particular, by means of the present invention, at least one analyte (target analyte) of a sample, preferably a nucleic-acid product, such as a particular nucleic-acid sequence, can be determined or detected. In particular, the sample can be tested for qualitatively or quantitatively determining at least one analyte, for example, in order for it to be possible to detect a disease and/or pathogen.

The present invention deals in particular with what are known as point-of-care systems, i.e., with systems, devices and other apparatuses, and deals with methods for carrying out tests on a sample at the sampling site and/or independently or away from a central laboratory or the like.

Description of Related Art

U.S. Pat. No. 5,096,669 discloses a point-of-care system for testing a biological sample, in particular a blood sample. The system comprises a single-use cartridge and an analysis device. Once the sample has been received, the cartridge is inserted into the analysis device in order to carry out the test. The cartridge comprises a microfluidic system and a sensor apparatus comprising electrodes, the apparatus being calibrated by means of a calibration liquid and then being used to test the sample.

Furthermore, International Patent Application Publication WO 2006/125767 A1 and corresponding U.S. Pat. No. 9,110,044 disclose a point-of-care system for integrated and automated DNA or protein analysis, comprising a single-use cartridge and an analysis device for fully automatically processing and evaluating molecular-diagnostic analyzes using the single-use cartridge. The cartridge is designed to receive a sample, in particular blood, and in particular allows cell disruption, PCR and detection of PCR amplification products, which are bonded to capture molecules and provided with a label enzyme, in order for it to be possible to detect bonded PCR amplification products or nucleic sequences as target analytes in what is known as a redox cycling process.

U.S. Patent Application Publication 2014/0377852 A1 discloses a microfluidic device for performing protein assays and/or nucleic acid assays, wherein glass nano-reactors formed by functionalized micro-length tubes are used for optical detection. The glass nano-reactors can be provided with captures strands complementary to a sequence of interest. Multiple different populations of glass nano-reactors, specific for different DNA target populations can be used.

SUMMARY OF THE INVENTION

The problem addressed by the present invention is to provide an improved method and an improved analysis system for testing a sample, with efficient, rapid, reliable and/or cost-effective testing of the sample and/or measurement or detection of different analytes being made possible or being assisted.

The above problem is solved by a method and a system as described herein.

One aspect of the present invention involves bonding the different nucleic-acid sequences and/or products of a sample to corresponding capture molecules at different hybridization temperatures, and/or varying the hybridization temperature of preferably amplified analytes and/or amplification products in order to bond to capture molecules, in particular on or in a sensor apparatus, and/or bonding different, preferably amplified analytes and/or amplification products in succession at different hybridization temperatures.

Particularly preferably, a first group of amplification products, in particular of a first analyte, a second group of other amplification products, in particular of a second analyte, and an optional third group of yet other amplification products, in particular of a third analyte, are bonded to the corresponding capture molecules of the sensor apparatus at different hybridization temperatures.

Preferably, the sensor apparatus comprises a sensor compartment and the amplification products and/or different groups are bonded in the (same) sensor compartment to the corresponding capture molecules at different hybridization temperatures. This allows in particular a very compact and simple realization and/or detection or identification of a multiplicity of analytes, amplification products and/or groups by means of or within one sensor apparatus or sensor compartment.

The analytes and/or amplification products bonded at different hybridization temperatures are preferably detected in a single or common detection process.

Particularly preferably, the sensor apparatus is only used a single time for a process for detecting said analytes and/or amplification products, electrochemical determination preferably taking place in particular simultaneously for all the bonded amplification products. This allows very rapid and efficient testing.

It is proposed that different analytes and/or amplification products of different analytes can be very efficiently bonded in succession by hybridization temperatures, to preferably immobilized capture molecules, particularly preferably on or in a sensor apparatus, in order for it to be possible to measure and/or determine or detect a particularly large number of different amplification products at the same time, in particular in a single or common detection process.

In the context of the present invention, it is thus possible to test analytes and/or amplification products, that are produced and/or amplified in parallel and have different hybridization temperatures, in a single detection process and at the same time with high specificity.

Preferably, different analytes and/or amplification products or groups thereof are initially, in particular simultaneously and/or in parallel, produced by means of an amplification reaction, in particular PCR, in preferably different PCR chambers and/or reaction cavities, and are then bonded to the capture molecules in succession at different hybridization temperatures.

In particular, it is provided that the first, second and optional third group are produced in different reaction cavities. It may however also be provided that the analytes are amplified by means of an amplification reaction, in particular PCR, in a common PCR chamber and/or reaction cavity, and/or that the amplification products are produced in a common reaction cavity, and the subsequent hybridization to the capture molecules is carried out at different, in particular decreasing, hybridization temperatures.

Preferably, a plurality of amplification reactions, in particular PCRs, run simultaneously, in parallel or independently from one another during the test.

Preferably, different amplification reactions, in particular PCRs with different primers, are provided or carried out.

Within the meaning of the present invention, amplification reactions are in particular molecular-biological reactions in which an analyte is amplified/copied and/or in which amplification products, in particular nucleic-acid products, of an analyte are produced. Particularly preferably, PCRs are amplification reactions within the meaning of the present invention.

"PCR" stands for polymerase chain reaction and is a molecular-biological method by means of which certain analytes, in particular portions of RNA or DNA, of a sample are amplified, preferably in several cycles, using polymerases or enzymes, in particular in order to then test and/or detect the amplification products or nucleic-acid products. If RNA is intended to be tested and/or amplified, before the PCR is carried out, a cDNA is produced starting from the RNA, in particular using reverse transcriptase. The cDNA is used as a template for the subsequent PCR.

Preferably, during a PCR, a sample is first denatured by the addition of heat in order to separate the strands of DNA or cDNA. Preferably, primers or nucleotides are then deposited on the separated single strands of DNA or cDNA, and a desired DNA or cDNA sequence is replicated by means of polymerase and/or the missing strand is replaced by means of polymerase. This process is preferably repeated in a plurality of cycles until the desired quantity of the DNA or cDNA sequence is available.

For the PCR, marker primers are preferably used, i.e. primers which (additionally) produce a marker or a label, in particular biotin, on the amplified analyte. This allows or facilitates detection. Preferably, the primers used are biotinylated and/or comprise or form in particular covalently bonded biotin as the label.

The proposed analysis system for testing an in particular biological sample preferably comprises a sensor apparatus for detecting nucleic-acid sequences and/or in particular amplified analytes and/or amplification products, the sensor apparatus preferably comprising immobilized capture molecules for bonding the sequences, analytes and/or amplification products.

According to another aspect of the present invention, which can also be implemented independently, the capture molecules have different hybridization temperatures and/or the capture molecules are designed to hybridize to the corresponding sequences, analytes and/or amplification products at different hybridization temperatures. This results in corresponding advantages.

Preferably, the sensor apparatus comprises a sensor compartment, wherein the capture molecules are arranged or immobilized in the (same) sensor compartment of the sensor apparatus so that the different analytes, amplification products and/or groups can be bonded within the (same) sensor apparatus or sensor compartment at different hybridization temperatures. This allows in particular a very compact and simple realization and/or detection or identification of a multiplicity of analytes, amplification products and/or groups by means of or within one sensor apparatus or sensor compartment.

The hybridization temperature is preferably the (average) temperature at which an (amplified) analyte, in particular portions of RNA or DNA, and/or an amplification product is bonded to corresponding capture molecules and/or is hybridized to corresponding capture molecules.

The optimal hybridization temperature is preferably the temperature at which the number of amplification products bonded to corresponding capture molecules is maximized and/or the number of amplification products bonded to one another is minimized.

Preferably, the (optimal) hybridization temperature varies for different analytes and/or amplification products.

A group of different analytes and/or amplification products preferably only includes, at least substantially, analytes and/or amplification products having similar (optimal) hybridization temperatures. Therefore, this results in an average and/or optimal hybridization temperature of the group or a temperature range of (optimal) hybridization temperatures. At this temperature or in this temperature range of the group—both also referred to as "group temperature" for short—the total number of analytes and/or amplification products in this group that are bonded to the capture molecules is (likely to be) maximal. The temperature range is preferably less than 8° C., in particular less than 5° C.

Preferably, different groups having different group temperatures are formed. The group temperatures preferably differ or are spaced apart by about 1° C. or more, preferably at least 2° C., in particular by more than 3° C.

In particular, the group temperature of a first group is greater than the group temperature of a second group.

Preferably, the (optimal) hybridization temperature varies depending on the GC content of the DNA or cDNA, the length of the DNA or cDNA, the melting point or melting temperature of the DNA or cDNA sequence and/or the conditioning or salt concentration of the solvent, ambient medium and/or buffer.

The melting point or melting temperature is preferably the temperature at which or from which the DNA or cDNA denatures and/or the strands of double-stranded DNA or cDNA are separated from one another. The melting point or melting temperature is preferably dependent on the GC content of the DNA or cDNA, the length of the DNA or cDNA, and/or the conditioning or salt concentration of the solvent, ambient medium and/or buffer. Preferably, the melting point or melting temperature is at least 85° C. or 90° C., particularly preferably 92° C. or 94° C., and/or at most 99° C. or 98° C., particularly preferably at most 97° C. or 96° C.

Preferably, the hybridization temperature is lower than the melting point or melting temperature, preferably by at least 2° C. or 5° C., particularly preferably 8° C. or 10° C., in particular 15° C. or 20° C. or more.

The capture molecules are in particular oligonucleotide probes, which are preferably immobilized on the sensor, sensor array and/or electrodes preferably by a spacer, in particular a C6 spacer. The formation of structures that disrupt hybridization, e.g., hairpin structures, can be prevented by the preferred bonding of the capture molecules by spacers.

Within the meaning of the present invention, the term "detector molecules" is preferably understood to mean molecules that bond specifically to the marker or label of the primers used to amplify the analytes and/or analytes or amplification products provided therewith, and thus allow the detection thereof.

In particular, the detector molecules may be enzyme conjugates and/or immunoconjugates, which bond specifically to the marker or label, in particular biotin, and comprise a reporter enzyme for converting a substrate.

In the context of the present invention, the detector molecules are preferably based on streptavidin, which has a high affinity for biotin, and/or alkaline phosphatase, which can convert non-reactive phosphate monoesters to electrochemically active molecules and phosphate.

Preferably, a detection system is used, where the label is based on biotin and where the detector molecules are based on streptavidin/alkaline phosphatase. However, other detector molecules can also be used.

The analysis system is in particular portable, mobile and/or is a point-of-care system and/or can be used in particular at the sampling site and/or away from a central laboratory.

The analysis system preferably comprises an analysis device and/or at least one cartridge for testing the sample.

The term "analysis device" is preferably understood to mean an instrument which is in particular mobile and/or can be used on site, and/or which is designed to chemically, biologically and/or physically test and/or analyze a sample or a component thereof, preferably in and/or by means of a cartridge. In particular, the analysis device controls the testing of the sample in the cartridge.

Particularly preferably, the analysis device is designed to receive the cartridge or to connect said cartridge.

The term "cartridge" is preferably understood to mean a structural apparatus or unit designed to receive, to store, to physically, chemically and/or biologically treat and/or prepare and/or to measure a sample, preferably in order to make it possible to detect, identify or determine at least one analyte of the sample.

A cartridge within the meaning of the present invention preferably comprises a fluid system having a plurality of channels, cavities and/or valves for controlling the flow through the channels and/or cavities.

In particular, within the meaning of the present invention, a cartridge is designed to be at least substantially planar and/or card-like, in particular is designed as a (micro)fluidic card and/or is designed as a main body or container that can preferably be closed and/or said cartridge can be inserted and/or plugged into a proposed analysis device when it contains the sample.

The above-mentioned aspects and features of the present invention and the aspects and features of the present invention twill become apparent from the following description and can, in principle, be implemented independently from one another, but also in any combination or order.

Other aspects, advantages, features and properties of the present invention will also become apparent from the following description of a preferred embodiment with reference to the accompanying drawings.

DETAILED DESCRIPTION OF THE INVENTION

In the figures, which are only schematic and sometimes not to scale, the same reference signs are used for the same or similar parts and components, corresponding or comparable properties and advantages being achieved even if these are not repeatedly described.

Figure 1:
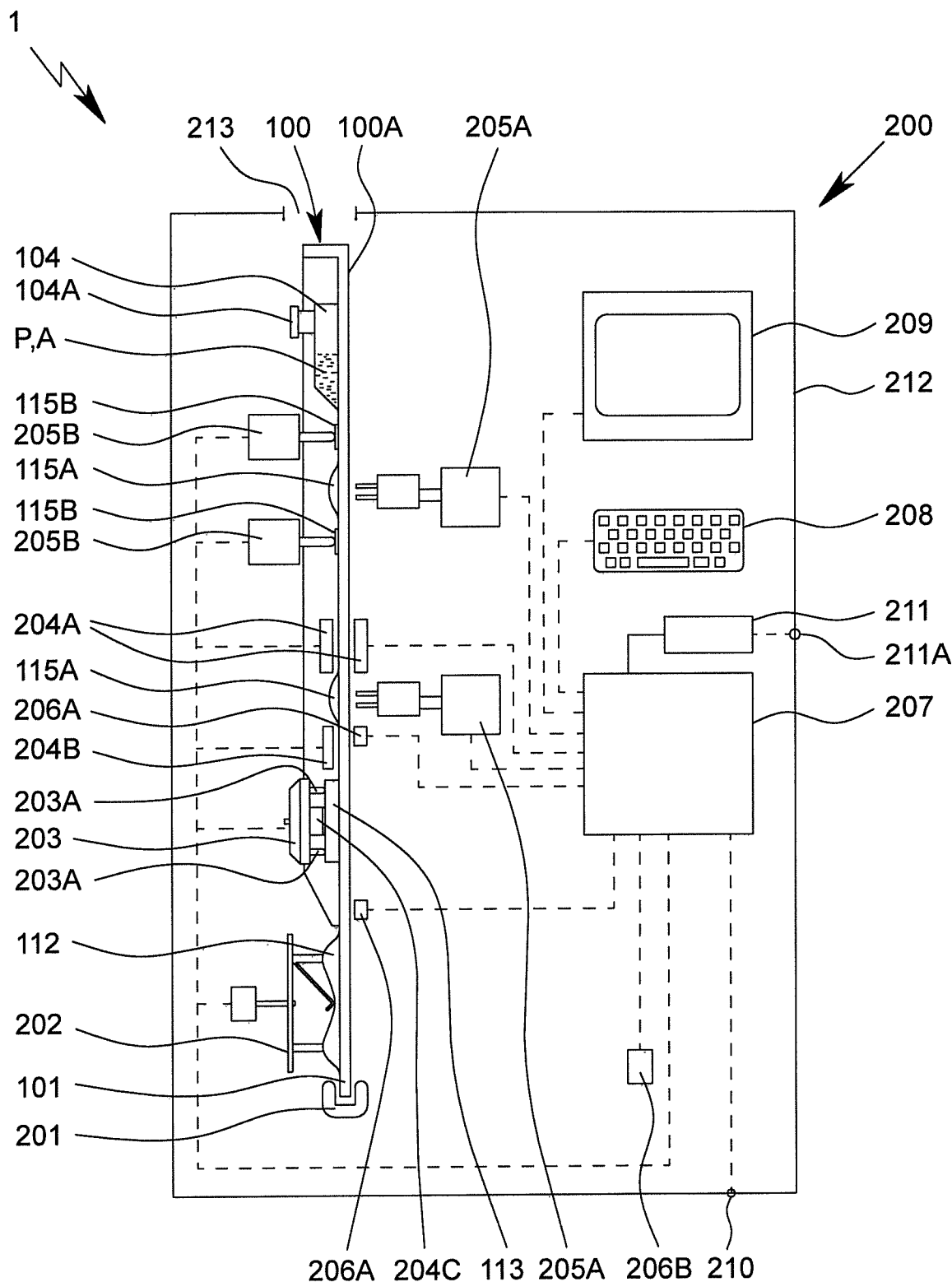
FIG. 1 is a schematic section through a proposed analysis system or analysis device comprising a proposed cartridge received therein.

FIG. 1 is a highly schematic view of a proposed analysis system 1 and analysis device 200 for testing, in particular. a biological sample P, preferably by means of or in an apparatus or cartridge 100.

Figure 2:
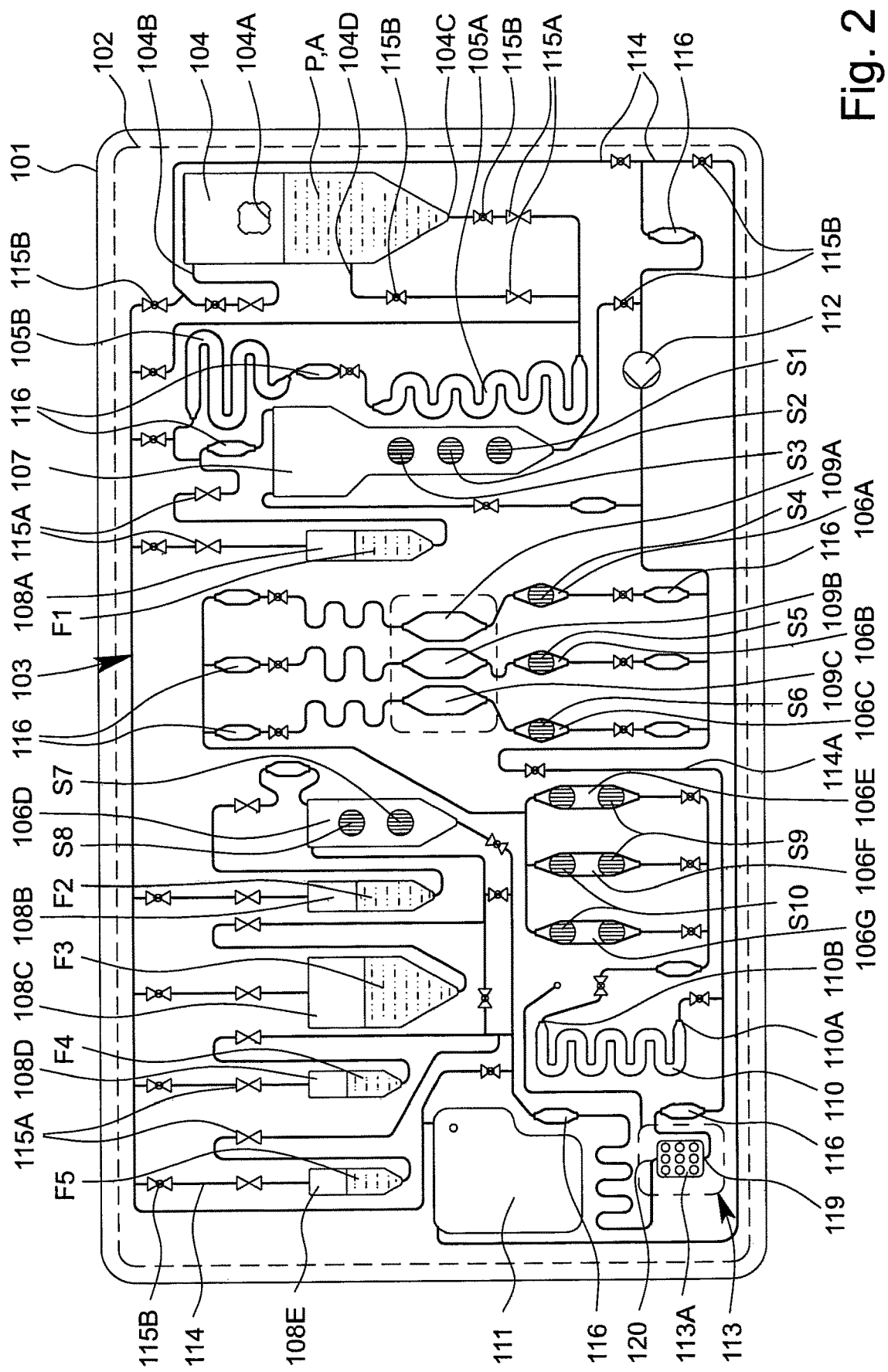
FIG. 2 is a schematic view of the cartridge.

FIG. 2 is a schematic view of a preferred embodiment of the proposed apparatus or cartridge 100 for testing the sample P. The apparatus or cartridge 100, in particular, forms a handheld unit, and in the following is merely referred to as a cartridge.

The term "sample" is preferably understood to mean the sample material to be tested, which is in particular taken from a human or animal. In particular, within the meaning of the present invention, a sample is a fluid, such as saliva, blood, urine or another liquid, preferably from a human or animal, or a component thereof. Within the meaning of the present invention, a sample may be pretreated or prepared if necessary, or may come directly from a human or animal or the like, for example. A food sample, environmental sample or another sample may optionally also be tested, in particular for environmental analytics, food safety and/or for detecting other substances, preferably natural substances, but also biological or chemical warfare agents, poisons or the like.

Preferably, the analysis system 1 or analysis device 200 controls the testing of the sample P in particular in or on the cartridge 100 and/or is used to evaluate the testing or the collection, processing and/or storage of measured values from the test.

By means of the proposed analysis system 1 or analysis device 200 or by means of the cartridge 100 and/or using the proposed method for testing the sample P, preferably an analyte A of the sample P, in particular a nucleic-acid product, such as a certain nucleic-acid sequence, or particularly preferably a plurality of analytes A of the sample P, can be determined, identified or detected. Said analytes are in particular detected and/or measured not only qualitatively, but particularly preferably also quantitatively.

Therefore, the sample P can in particular be tested for qualitatively or quantitatively determining at least one analyte A, for example, in order for it to be possible to detect a disease and/or pathogen or to determine other values, which are important for diagnostics, for example.

Particularly preferably, a molecular-biological test is made possible by means of the analysis system 1 and/or analysis device 200 and/or by means of the cartridge 100.

Particularly preferably, a molecular and/or PCR assay, in particular for detecting DNA and/or RNA, i.e., nucleic-acid products and/or sequences, is made possible and/or carried out.

Preferably, the sample P or individual components of the sample P or analytes A can be amplified if necessary, in particular by means of PCR, and tested, identified or detected in the analysis system 1, analysis device 200 and/or in the cartridge 100. Preferably, amplification products V of the analyte A or analytes A are thus produced.

The analytes A and/or amplification products V of the sample P, in particular the nucleic-acid products, which are amplified in particular by means of PCR, in particular have a length of at least 20 or 50, particularly preferably 80 or 100, and/or at most 300 or 280, particularly preferably 250 or 220, nucleotides. However, it may also be provided that shorter or longer amplification products V are produced in particular by means of PCR.

In the following, further details are first given on a preferred construction of the cartridge 100, with features of the cartridge 100 preferably also directly representing features of the analysis system 1, in particular even without any further explicit explanation.

The cartridge 100 is preferably at least substantially planar, flat and/or plate-shaped and/or card-shaped.

The cartridge 100 preferably comprises, in particular, an at least substantially flat, planar, plate-shaped and/or card-like main body 101, the main body 101 in particular being made of and/or injection-molded from plastics material, particularly preferably polypropylene.

The cartridge 100 preferably comprises at least one film or cover 102 for covering the main body 101 and/or cavities and/or channels formed therein at least in part, in particular on the front 100A, and/or for forming valves or the like, the cover being shown by dashed lines in FIG. 2.

The analysis system 1 or cartridge 100 or the main body 101 thereof, in particular together with the cover 102, preferably forms and/or comprises a fluidic system 103, referred to in the following as the fluid system 103.

The cartridge 100 and/or the fluid system 103 thereof is preferably at least substantially vertically oriented in the operating position and/or during the test, in particular in the analysis device 200, as shown schematically in FIG. 1. In particular, the main plane or surface extension of the cartridge 100 thus extends at least substantially vertically in the operating position.

The cartridge 100 and/or the fluid system 103 preferably comprises a plurality of cavities, in particular at least one receiving cavity 104, at least one metering cavity 105, at least one intermediate cavity 106, at least one mixing cavity 107, at least one storage cavity 108, at least one reaction cavity 109, at least one intermediate temperature-control cavity 110 and/or at least one collection cavity 111, as shown in FIG. 1.

The cartridge 100 and/or the fluid system 103 also preferably comprises at least one pump apparatus 112 and/or at least one sensor apparatus 113.

Some, most or all of the cavities are preferably formed by chambers and/or channels or other depressions in the cartridge 100 and/or the main body 101, and particularly preferably are covered or closed by the film or cover 102. However, other structural solutions are also possible.

In the example shown, the cartridge 100 or the fluid system 103 preferably comprises two metering cavities 105A and 105B, a plurality of intermediate cavities 106A to 106G, a plurality of storage cavities 108A to 108E and/or a plurality of reaction cavities 109, which can preferably be loaded independently from one another, in particular a first reaction cavity 109A, a second reaction cavity 109B and an optional third reaction cavity 109C, as can be seen in FIG. 2.

The reaction cavity/cavities 109 is/are used in particular to carry out an amplification reaction, in particular PCR, or several, preferably different, amplification reactions, in particular PCRs. It is preferable to carry out several, preferably different, PCRs, i.e., PCRs having different primer combinations or primer pairs, in parallel and/or independently and/or in different reaction cavities 109.

The amplification products V and/or other portions of the sample P forming in the one or more reaction cavities 109 can be conducted or fed to the connected sensor apparatus 113, in particular by means of the pump apparatus 112.

The sensor apparatus 113 is used in particular for detecting, particularly preferably qualitatively and/or quantitatively determining, the analyte A or analytes A of the sample P, in this case particularly preferably the amplification products V of the analytes A. Alternatively or additionally, however, other values may also be collected or determined.

In particular, the pump apparatus 112 comprises or forms a tube-like or bead-like raised portion, in particular by means of the film or cover 102, particularly preferably on the back of the cartridge, as shown schematically in FIG. 1.

The cartridge 10Q, the main body 101 and/or the fluid system 103 preferably comprise a plurality of channels 114 and/or valves 115, as shown in FIG. 2.

By means of the channels 114 and/or valves 115, the cavities 104 to 111, the pump apparatus 112 and/or the sensor apparatus 113 can be temporarily and/or permanently connected and/or separated from one another, as required and/or optionally or selectively, in particular such that they are controlled by the analysis system 1 or the analysis device 200.

The cavities 104 to 111 are preferably each fluidically linked by a plurality of channels 114. Particularly preferably, each cavity is linked or connected by at least two associated channels 114, in order to make it possible for fluid to fill, flow through and/or drain from the respective cavities as required.

The fluid transport or the fluid system 103 is preferably not based on capillary forces, or is not exclusively based on said forces, but in particular is essentially based on the effects of gravity and/or pumping forces and/or compressive forces and/or suction forces that arise, which are particularly preferably generated by the pump or pump apparatus 112. In this case, the flows of fluid or the fluid transport and the metering are controlled by accordingly opening and closing the valves 115 and/or by accordingly operating the pump or pump apparatus 112, in particular by means of a pump drive 202 of the analysis device 200.

Preferably, each of the cavities 104 to 110 has an inlet at the top and an outlet at the bottom in the operating position. Therefore, if required, only liquid from the respective cavities can be removed via the outlet.

In particular, the liquid-containing cavities, particularly preferably the storage cavity/cavities 108, the mixing cavity 107 and/or the receiving cavity 104, are each dimensioned such that, when said cavities are filled with liquid, bubbles of gas or air that may potentially form rise upwards in the operating position, such that the liquid collects above the outlet without bubbles. However, other solutions are also possible here.

Preferably, at least one valve 115 is assigned to each cavity, the pump apparatus 112 and/or the sensor apparatus 113 and/or is arranged upstream of the respective inlets and/or downstream of the respective outlets.

Preferably, the cavities 104 to 111 or sequences of cavities 104 to 111, through which fluid flows in series or in succession for example, can be selectively released and/or fluid can selectively flow therethrough by the assigned valves 115 being actuated, and/or said cavities can be fluidically connected to the fluid system 103 and/or to other cavities.

In particular, the valves 115 are formed by the main body 101 and the film or cover 102 and/or are formed in another manner, for example by additional layers, depressions or the like.

Particularly preferably, one or more valves 115A are provided which are preferably tightly closed initially or when in storage, particularly preferably in order to seal liquids or liquid reagents F, located in the storage cavities 108, and/or the fluid system 103 from the open receiving cavity 104 in a storage-stable manner.

Preferably, an initially closed valve 115A is arranged upstream and downstream of each storage cavity 108. Said valves are preferably only opened, in particular automatically, when the cartridge 100 is actually being used and/or while inserting the cartridge 100 into the analysis device 200.

A plurality of valves 115A, in particular three valves in this case, are preferably assigned to the receiving cavity 104 when an optional intermediate connection 104D is provided in addition to an inlet 104B and an outlet 104C, for example in order for it to be possible to optionally discharge or remove a supernatant of the sample P, such as blood serum or the like. Depending on the use, in addition to the valve 115A on the inlet 104B, then preferably only the valve 115A either at the outlet 104C or at the intermediate connection 104D is opened.

The valves 115A assigned to the receiving cavity 104 seal the fluid system 103 and/or the cartridge 100 in particular fluidically and/or in a gas-tight manner until the sample P is inserted and the receiving cavity 104 or a connection 104A of the receiving cavity 104 is closed.

As an alternative or in addition to the valves 115A (which are initially closed), one or more valves 115B are preferably provided which are not closed in a storage-stable manner and/or which are open initially and/or which can be closed by actuation. These valves are used in particular to control the flows of fluid during the test.

The cartridge 10Q is preferably designed as a microfluidic card and/or the fluid system 103 is preferably designed as a microfluidic system. In the present invention, the term "microfluidic" is preferably understood to mean that the respective volumes of individual cavities, some of the cavities or all of the cavities 104 to 111 and/or channels 114 are, separately or cumulatively, less than 5 ml or 2 ml, particularly preferably less than 1 ml or 800 μl, in particular less than 600 μl or 300 μl, more particularly preferably less than 200 μl or 100 μl.

Particularly preferably, a sample P having a maximum volume of 5 ml, 2 ml or 1 ml can be introduced into the cartridge 100 and/or the fluid system 103, in particular the receiving cavity 104.

Reagents and liquids which are preferably introduced or provided before the test in liquid form as liquids or liquid reagents F and/or in dry form as dry reagents S are required for testing the sample P, as shown in the schematic view according to FIG. 2.

Furthermore, other liquids F, in particular in the form of a wash buffer, solvent for dry reagents S or a substrate SU, for example in order to form detection molecules and/or a redox system, are also preferably required for the test, the detection process and/or for other purposes and are in particular provided in the cartridge 10Q, i.e., are likewise introduced before use, in particular before delivery. At some points in the following, a distinction is not made between liquid reagents and other liquids, and therefore the respective explanations are accordingly also mutually applicable.

The analysis system 1 or the cartridge 100 preferably contains all the reagents and liquids required for carrying out one or more amplification reactions or PCRs and/or for carrying out the test, and therefore, particularly preferably, it is only necessary to receive the optionally pretreated sample P.

The cartridge 100 and/or the fluid system 103 preferably comprises a bypass 114A that can optionally be used, in order for it to be possible, if necessary, to conduct or convey the sample P or components thereof past the reaction cavities 109 and, by passing the optional intermediate temperature-control cavity 110, also directly to the sensor apparatus 113, and/or in order for it to be possible to convey or pump liquids or liquid reagents F2-F5 out of the storage cavities 108B-108E into the sensor apparatus 113, in particular in the opposite direction to the analytes A and/or amplification products V, when the bypass 114A is open, more specifically when the valve 115B of the bypass 114A is open.

The cartridge 100 or the fluid system 103 or the channels 114 preferably comprise sensor portions 116 or other apparatuses for detecting liquid fronts and/or flows of fluid.

It is noted that various components, such as the channels 114, the valves 115, in particular the valves 115A that are initially closed and the valves 115B that are initially open, and the sensor portions 116 in FIG. 2 are, for reasons of clarity, only labelled in some cases, but the same symbols are used in FIG. 2 for each of these components.

The collection cavity 111 is preferably used for receiving excess or used reagents and liquids and volumes of the sample. It is preferably given appropriate large dimensions and/or is only provided with inputs or inlets, in particular such that liquids cannot be removed or pumped out again in the operating position.

The receiving cavity 104 preferably comprises a connection 104A for introducing the sample P. After the sample P is introduced into the receiving cavity 104, said cavity and/or the connection 104A is closed.

The cartridge 100 can then be inserted into the proposed analysis device 200 and/or received thereby, as shown in FIG. 1, in order to test the sample P. Alternatively, the sample P could also be fed in later.

FIG. 1 shows the analysis system 1 in a ready-to-use state for carrying out a test on the sample P received in the cartridge 100. In this state, the cartridge 100 is therefore linked to, received by and/or inserted into the analysis device 200.

In the following, some features and aspects of the analysis device 200 are first explained in greater detail. The features and aspects relating to said device are preferably also directly features and aspects of the proposed analysis system 1, in particular even without any further explicit explanation.

The analysis system 1 or analysis device 200 preferably comprises a mount or receptacle 201 for mounting and/or receiving the cartridge 100.

Preferably, the cartridge 100 is fluidically, in particular hydraulically, separated or isolated from the analysis device 200. In particular, the cartridge 100 forms a preferably independent and in particular closed fluidic and/or hydraulic system 103 for the sample P and the reagents and other liquids.

Preferably, the analysis device 200 is designed to actuate the pump apparatus 112 and/or valves 115, to have a thermal effect and/or to detect measured data, in particular by means of the sensor apparatus 113 and/or sensor portions 116.

The analysis system 1 or analysis device 200 preferably comprises a pump drive 202, the pump drive 202 in particular being designed for mechanically actuating the pump apparatus 112.

Preferably, a head of the pump drive 202 can be rotated in order to rotationally axially depress the preferably bead-like raised portion of the pump apparatus 112. Particularly preferably, the pump drive 202 and pump apparatus 112 together form a pump, in particular in the manner of a hose pump or peristaltic pump and/or a metering pump, for the fluid system 103 and/or the cartridge 100.

Particularly preferably, the pump is constructed as described in DE 10 2011 015 184 B4 and corresponding U.S. Pat. No. 8,950,424. However, other structural solutions are also possible.

Preferably, the capacity and/or discharge rate of the pump can be controlled and/or the conveying direction of the pump and/or pump drive 202 can be switched. Preferably, fluid can thus be pumped forwards or backwards as desired.

The analysis system 1 or analysis device 200 preferably comprises a connection apparatus 203 for in particular electrically and/or thermally connecting the cartridge 100 and/or the sensor apparatus 113.

As shown in FIG. 1, the connection apparatus 203 preferably comprises a plurality of electrical contact elements 203A, the cartridge 100, in particular the sensor apparatus 113, preferably being electrically connected or connectable to the analysis device 200 by the contact elements 203A.

The analysis system 1 or analysis device 200 preferably comprises one or more temperature-control apparatuses 204, in particular heating elements or Peltier elements, for temperature-controlling the cartridge 100 and/or having a thermal effect on the cartridge 100, in particular for heating and/or cooling.

Individual temperature-control apparatuses 204, some of these apparatuses or all of these apparatuses can preferably be positioned against the cartridge 100, the main body 101, the cover 102, the sensor apparatus 113 and/or individual cavities and/or can be thermally coupled thereto and/or can be integrated therein and/or in particular can be operated or controlled electrically by the analysis device 200. In the example shown, in particular the temperature-control apparatuses 204A, 204B and/or 204C are provided.

Preferably, the temperature-control apparatus 204A, referred to in the following as the reaction temperature-control apparatus 204A, is assigned to the reaction cavity 109 or to a plurality of reaction cavities 109, in particular in order for it to be possible to carry out one or more amplification reactions and/or PCRs therein.

The reaction cavities 109 are preferably temperature-controlled simultaneously and/or uniformly, in particular by means of one common reaction temperature-control apparatus 204A or two reaction temperature-control apparatuses 204A.

More particularly preferably, the reaction cavity/cavities 109 can be temperature-controlled from two different sides and/or by means of two or the reaction temperature-control apparatuses 204A that are preferably arranged on opposite sides.

Alternatively, for reaction cavities 109, each reaction cavity 109 can be temperature-controlled independently and/or individually.

The temperature-control apparatus 204B, referred to in the following as the intermediate temperature-control apparatus 204B, is preferably assigned to the intermediate temperature-control cavity 110 and/or is designed to temperature-control the intermediate temperature-control cavity 110 or a fluid located therein, in particular the amplification products V, preferably to a preheat temperature TV.

The intermediate temperature-control cavity 110 and/or temperature-control apparatus 204B is preferably arranged upstream of or (immediately) before the sensor apparatus 113, in particular in order for it to be possible to temperature-control or preheat, in a desired manner, fluids to be fed to the sensor apparatus 113, in particular analytes A and/or amplification products V, particularly preferably immediately before said fluids are fed.

Particularly preferably, the intermediate temperature-control cavity 110 and/or temperature-control apparatus 204B is designed or intended to denature the sample P or analytes A and/or the amplification products V produced, and/or to divide any double-stranded analytes A or amplification products V into single strands and/or to counteract premature bonding and/or hybridizing of the amplification products V, in particular by the addition of heat.

The intermediate temperature-control cavity 110 is preferably elongate and/or designed as a channel which is in particular sinuous or meandering and/or planar in cross section. Advantageously, a sufficiently long retention time of the fluid and/or sufficiently great thermal coupling with the fluid in the intermediate temperature-control cavity 110 is thus obtained in order to achieve the desired temperature control for example without changing the flow speed or also while the fluid is flowing through said cavity. However, other solutions are also possible here, in particular those in which the fluid flow in the intermediate temperature-control cavity 110 is stopped.

Preferably, the length of the intermediate temperature-control cavity 110 is at least 10 mm or 15 mm, particularly preferably at least 20 mm or 25 mm, in particular 30 mm or 40 mm, and/or at most 80 mm or 75 mm, particularly preferably at most 70 mm or 65 mm, in particular at most 60 mm.

Preferably, the intermediate temperature-control cavity 110 has a volume of at least 10 µl or 20 µl, particularly preferably at least 25 µl or 30 µl, and/or at most 500 µl or 400 µl, particularly preferably at most 350 µl or 300 µl.

The intermediate temperature-control cavity 110 comprises an inlet 110A and an outlet 110B, a valve 115, in particular an initially open valve 115A, preferably being assigned to (each of) the inlet 110A and/or the outlet 110B, as shown in FIG. 1. In this way, the flow of fluid through the intermediate temperature-control cavity 110 can be controlled. For example, it is thus possible to temperature-control a fluid flowing through the intermediate temperature-control cavity 110 while it is flowing through and/or to initially fill the intermediate temperature-control cavity 110 with a fluid to be temperature-controlled and to close the input-side and/or output-side valve 115A in order to stop the fluid in the intermediate temperature-control cavity 110 for the purpose of temperature control and to only subsequently pass on said fluid.

Preferably, the intermediate temperature-control cavity 110 is (fluidically) arranged between the reaction cavity/cavities 109 and the sensor apparatus 113 and/or (all) the reaction cavities 109 are fluidically connected or connectable to the sensor apparatus 113, preferably exclusively, by means of the intermediate temperature-control cavity 110.

Preferably, the intermediate temperature-control cavity 110 is arranged closer to the sensor apparatus 113 than to the reaction cavity/cavities 109. In particular, the distance or flow path between the intermediate temperature-control cavity 110, in particular the outlet 110B thereof, and the sensor apparatus 113 is shorter than the distance or flow path between the intermediate temperature-control cavity 110, in particular the inlet 110A thereof, and the reaction cavity/cavities 109.

The intermediate temperature-control cavity 110 is preferably designed to actively temperature-control, particularly preferably to heat, fluids, in particular the amplification products V, preferably to a melting point or melting temperature, as explained in greater detail in the following.

The intermediate temperature-control apparatus 204B assigned to the intermediate temperature-control cavity 110 is preferably designed to (actively) temperature control, in particular heat, the intermediate temperature-control cavity 110.

Preferably, the intermediate temperature-control apparatus 204B comprises a heating element, in particular a heating resistor or a Peltier element, or is formed thereby.

The intermediate temperature-control apparatus 204B is preferably planar and/or has a contact surface which is preferably elongate and/or rectangular allowing for heat transfer between the intermediate temperature-control apparatus 204B and the intermediate temperature-control cavity 110.

Preferably, the intermediate temperature-control apparatus 204B can be externally positioned against, in particular pressed against, the cartridge 100, the main body 101 and/or the cover 102, in the region of the intermediate temperature-control cavity 110 or on the intermediate temperature-control cavity 110, preferably over the entire surface thereof.

In particular, the analysis device 200 comprises the intermediate temperature-control apparatus 204B. However, other structural solutions are also possible in which the intermediate temperature-control apparatus 204B is arranged in the cartridge 100 or integrated in the cartridge 100, in particular in the intermediate temperature-control cavity 110.

Preferably, the analysis system 1, analysis device 200 and/or the cartridge 100 and/or one or each temperature-control apparatus 204 comprise/comprises a temperature detector and/or temperature sensor (not shown), in particular in order to make it possible to control and/or feedback control temperature.

One or more temperature sensors may for example be assigned to the sensor portions 116 and/or to individual channel portions or cavities, i.e. may be thermally coupled thereto.

Particularly preferably, a temperature sensor is assigned to each temperature-control apparatus 204A, 204B and/or 204C, for example in order to measure the temperature of the respective temperature-control apparatuses 204 and/or the contact surfaces thereof.

The temperature-control apparatus 204C, referred to in the following as the sensor temperature-control apparatus 204C, is in particular assigned to the sensor apparatus 113 and/or is designed to temperature-control fluids located in or on the sensor apparatus 113, in particular analytes A and/or amplification products V, reagents or the like, in a desired manner, preferably to a hybridization temperature TH.

The sensor temperature-control apparatus 204C preferably comprises a heating element, in particular a heating resistor or a Peltier element, or is formed thereby.

The sensor temperature-control apparatus 204C is preferably planar and/or has a contact surface which is preferably rectangular and/or corresponds to the dimensions of the sensor apparatus 113, the contact surface allowing for heat transfer between the sensor temperature-control apparatus 204C and the sensor apparatus 113.

Preferably, the analysis device 200 comprises the sensor temperature-control apparatus 204C. However, other structural solutions are also possible in which the sensor temperature-control apparatus 204C is integrated in the cartridge 100, in particular in the sensor apparatus 113.

Particularly preferably, the connection apparatus 203 comprises the sensor temperature-control apparatus 204C, and/or the connection apparatus 203 together with the sensor temperature-control apparatus 204C can be linked to, in particular pressed against, the cartridge 100, in particular the sensor apparatus 113.

More particularly preferably, the connection apparatus 203 and the sensor temperature-control apparatus 204C (together) can be moved toward and/or relative to the cartridge 100, in particular the sensor apparatus 113, and/or can be positioned against said cartridge, preferably in order to both electrically and thermally couple the analysis device 200 to the cartridge 100, in particular the sensor apparatus 113 or the support 113D thereof.

Preferably, the sensor temperature-control apparatus 204C is arranged centrally on the connection apparatus 203 or a support thereof and/or is arranged between the contact elements 203A.

In particular, the contact elements 203A are arranged in an edge region of the connection apparatus 203 or a support thereof or are arranged around the sensor temperature-control apparatus 204C, preferably such that the connection apparatus 203 is connected or connectable to the sensor apparatus 113 thermally in the center and electrically on the outside or in the edge region. However, other solutions are also possible here.

The analysis system 1 or analysis device 200 preferably comprises one or more actuators 205 for actuating the valves 115. Particularly preferably, different (types or groups of) actuators 205A and 205B are provided which are assigned to the different (types or groups of) valves 115A and 115B for actuating each of said valves, respectively.

The analysis system 1 or analysis device 200 preferably comprises one or more sensors 206. In particular, the sensors 206A are designed or intended to detect liquid fronts and/or flows of fluid in the fluid system 103. Particularly preferably, the sensors 206A are designed to measure or detect, for example optically and/or capacitively, a liquid front and/or the presence, the speed, the mass flow rate/volume flow rate, the temperature and/or another value of a fluid in a channel and/or a cavity, in particular in a respectively assigned sensor portion 116, which is in particular formed by a planar and/or widened channel portion of the fluid system 103.

Particularly preferably, the sensor portions 116 are each oriented and/or incorporated in the fluid system 103 and/or fluid flows against or through the sensor portions 116 such that, in the operating position of the cartridge 100, fluid flows through the sensor portions 116 in the vertical direction and/or from the bottom to the top, in order to make it possible or easier to reliably detect liquid.

Alternatively, or additionally, the analysis device 200 preferably comprises (other or additional) sensors 206B for detecting the ambient temperature, internal temperature, atmospheric humidity, position, and/or alignment, for example by means of a GPS sensor, and/or the orientation and/or inclination of the analysis device 200 and/or the cartridge 100.

The analysis system 1 or analysis device 200 preferably comprises a control apparatus 207, in particular comprising an internal clock or time base for controlling the sequence of a test and/or for collecting, evaluating and/or outputting or providing measured values in particular from the sensor apparatus 113, and/or from test results and/or other data or values.

The control apparatus 207 preferably controls or feedback controls the pump drive 202, the temperature-control apparatuses 204 and/or actuators 205, in particular taking into account or depending on the desired test and/or measured values from the sensor apparatus 113 and/or sensors 206.

Generally, it is noted that the cartridge 100, the fluid system 103 and/or the conveying of fluid preferably do not operate on the basis of capillary forces, but at least essentially or primarily under the effects of gravity and/or the effect of the pump or pump apparatus 112.

In the operating position, the liquids from the respective cavities are preferably removed, in particular drawn out, via the outlet that is at the bottom in each case, it being possible for gas or air to flow and/or be pumped into the respective cavities via the inlet that is in particular at the top. In particular, relevant vacuums in the cavities can thus be prevented or at least minimized when conveying the liquids.

The flows of fluid are controlled in particular by accordingly activating the pump or pump apparatus 112 and actuating the valves 115.

Particularly preferably, the pump drive 202 comprises a stepper motor, or a drive calibrated in another way, such that desired metering can be achieved, at least in principle, by means of appropriate activation.

Additionally, or alternatively, sensors 206A are preferably used to detect liquid fronts or flows of fluid, in particular in cooperation with the assigned sensor portions 116, in order to achieve the desired fluidic sequence and the desired metering by accordingly controlling the pump or pump apparatus 112 and accordingly activating the valves 115.

Optionally, the analysis system 1 or analysis device 200 comprises an input apparatus 208, such as a keyboard, a touch screen or the like, and/or a display apparatus 209, such as a screen.

The analysis system 1 or analysis device 200 preferably comprises at least one interface 210, for example, for controlling, for communicating and/or for outputting measured data or test results and/or for linking to other devices, such as a printer, an external power supply or the like. This may in particular be a wired or wireless interface 210.

The analysis system 1 or analysis device 200 preferably comprises a power supply 211, preferably a battery or an accumulator, which is in particular integrated and/or externally connected or connectable.

Preferably, an integrated accumulator is provided as a power supply 211 and is (re)charged by an external charging device (not shown) via a connection 211A and/or is interchangeable.

The analysis system 1 or analysis device 200 preferably comprises a housing 212, all the components and/or some or all of the apparatuses preferably being integrated in the housing 212. Particularly preferably, the cartridge 100 can be inserted or slid into the housing 212, and/or can be received by the analysis device 200, through an opening 213 which can in particular be closed, such as a slot or the like.

The analysis system 1 or analysis device 200 is preferably portable or mobile. Particularly preferably, the analysis device 200 weighs less than 25 kg or 20 kg, particularly preferably less than 15 kg or 10 kg, in particular less than 9 kg or 6 kg.

In the following, further details are given on a preferred construction of the sensor apparatus 113 with reference to FIG. 3 to FIG. 6.

The sensor apparatus 113 preferably allows electrochemical measurement and/or redox cycling.

In particular, the sensor apparatus 113 is designed to identify, to detect and/or to determine (identical or different) analytes A bonded to capture molecules M or products derived therefrom, in particular amplification products V of the analyte A or different analytes A.

Figure 3:
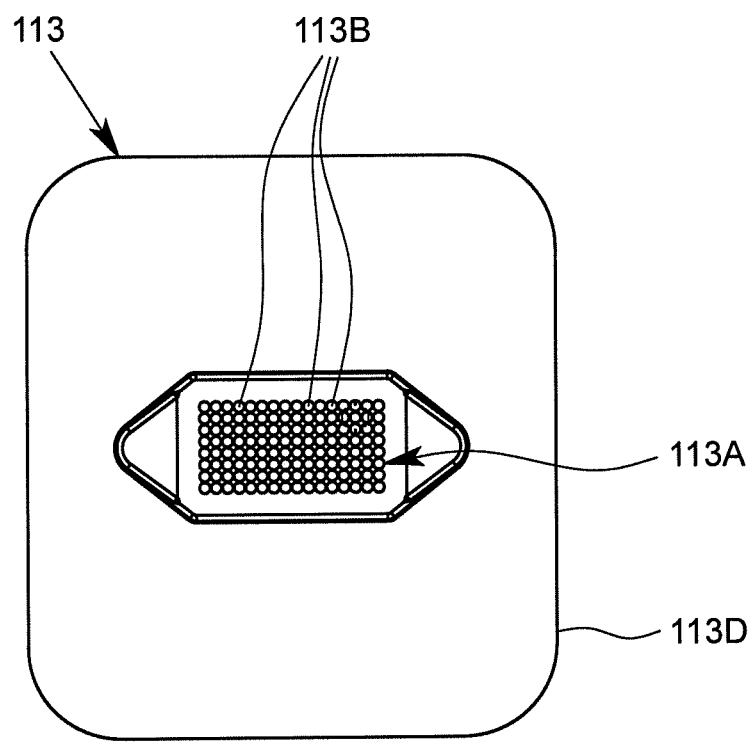
FIG. 3 is a schematic front view of a proposed sensor apparatus of the analysis system and/or cartridge.
Figure 4:
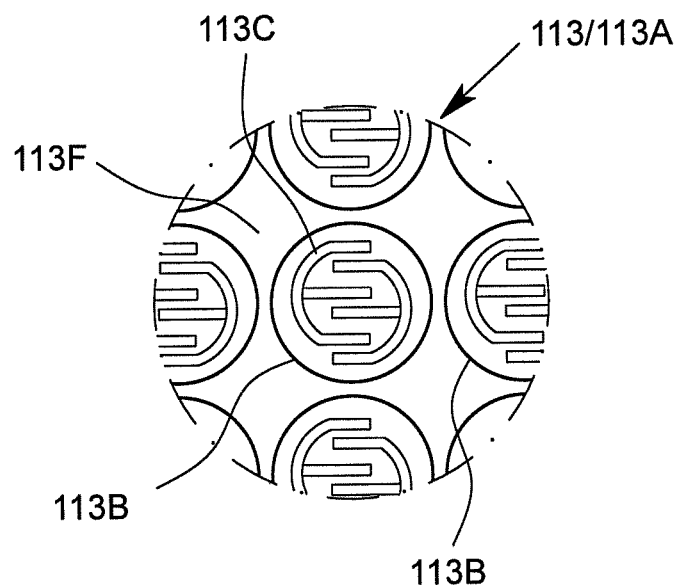
FIG. 4 is an enlarged detail from FIG. 3 illustrating a sensor field of the sensor apparatus.
Figure 5:
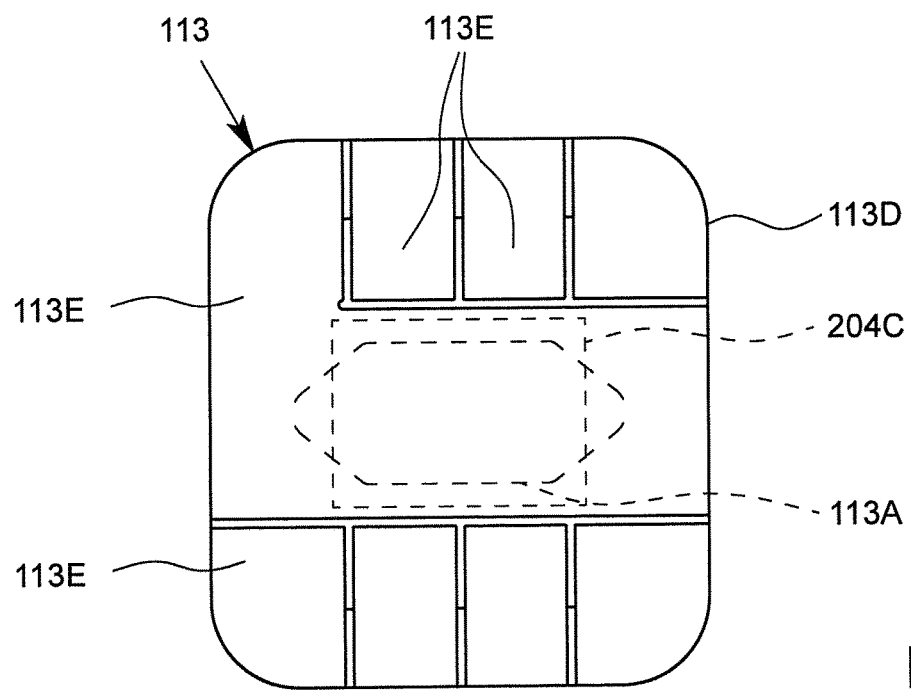
FIG. 5 is a schematic rear view of the sensor apparatus.
Figure 6:
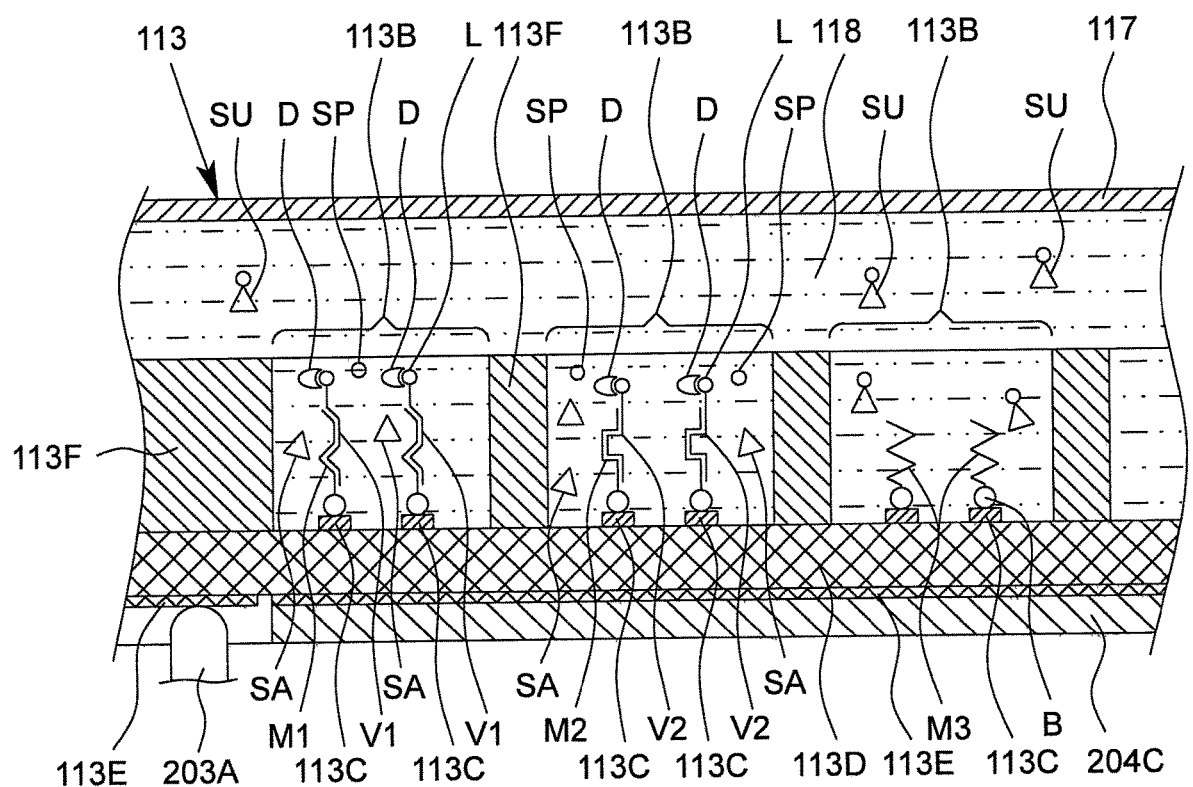
FIG. 6 is a schematic sectional view of the sensor apparatus.

The sensor apparatus 113 preferably comprises a sensor array 113A comprising a plurality of sensor regions or sensor fields 113B, as shown schematically in FIG. 3, which schematically shows the measuring side of the sensor apparatus 113 and/or the sensor array 113A. FIG. 4 is an enlarged detail from FIG. 3. FIG. 5 shows a connection side and FIG. 6 is a schematic section through the sensor apparatus 113.

Preferably, the sensor apparatus 113 or the sensor array 113A comprises more than 10 or 20, particularly preferably more than 50 or 80, in particular more than 100 or 120 and/or less than 1000 or 800 sensor fields 113B.

Preferably, the sensor apparatus 113 or the sensor array 113A comprises a plurality of electrodes 113C. At least two electrodes 113C are preferably arranged in each sensor region or sensor field 113B. In particular, at least two electrodes 113C in each case form a sensor field 113B.

The electrodes 113C are preferably made of metal, in particular of noble metal, such as platinum or gold, and/or said electrodes are coated, in particular with thiols.

Preferably, the electrodes 113C are finger-like and/or engage in one another, as can be seen from the enlarged detail of a sensor field 113B according to FIG. 4. However, other structural solutions or arrangements are also possible.

The sensor apparatus 113 preferably comprises a support 113D, in particular a chip, the electrodes 113C preferably being arranged on the support 113D and/or being integrated in the support 113D.

The measuring side comprises the electrodes 113C and/or is the side that faces the fluid, the sample P, the amplification products V and/or a sensor compartment, and/or is the side of the sensor apparatus 113 and/or the support 113D comprising capture molecules M (as shown in FIG. 6) to which the analytes A and/or amplification products V are bonded.

The connection side of the sensor apparatus 113 and/or the support 113D is preferably opposite the measuring side and/or is the side that faces away from the fluid, the sample P and/or the amplification product V.

Particularly preferably, the measuring side and the connection side of the sensor apparatus 113 and/or the support 113D each form one flat side of the in particular planar and/or plate-like support 113D.

The sensor apparatus 113, in particular the support 113D, preferably comprises a plurality of, in this case eight, electrical contacts or contact surfaces 113E, the contacts 113E preferably being arranged on the connection side and/or forming the connection side, as shown in FIG. 5.

Preferably, the sensor apparatus 113 can be contacted on the connection side and/or by means of the contacts 113E and/or can be electrically connected to the analysis device 200. In particular, an electrical connection can be established between the cartridge 100, in particular the sensor apparatus 113, and the analysis device 200, in particular the control apparatus 207, by electrically connecting the contacts 113E to the contact elements 203A.

Preferably, the contacts 113E are arranged laterally, in the edge region and/or in a plan view or projection around the electrodes 113C and/or the sensor array 113A, and/or the contacts 113E extend as far as the edge region of the sensor apparatus 113, in particular such that the support 113D can be electrically contacted, preferably by means of the connection apparatus 203 or the contact elements 203A, as already explained, laterally, in the edge region and/or around the sensor temperature-control apparatus 204C, which can preferably be positioned centrally or in the middle on the support 113D.

Preferably, the sensor fields 113B are separated from one another, as shown in the schematic view from FIG. 6. In particular, the sensor apparatus 113 comprises barriers or partitions between each of the sensor fields 113B, which are preferably formed by an in particular hydrophobic layer 113F having corresponding recesses for the sensor fields 113B. However, other structural solutions are also possible.

The cartridge 100 and/or the sensor apparatus 113 comprises or forms a sensor compartment 118. In particular, the sensor compartment 118 is formed between the sensor array 113A, the sensor apparatus 113 and/or the support 113D, or between the measuring side on one side and a sensor cover 117 on the other side.

The sensor apparatus 113 preferably defines the sensor compartment 118 by means of its measuring side and/or the sensor array 113A. The electrodes 113C are therefore in the sensor compartment 118.

Preferably, the cartridge 100 and/or the sensor apparatus 113 comprises the sensor cover 117, the sensor compartment 118 in particular being defined or delimited by the sensor cover 117 on the flat side.

Particularly preferably, the sensor cover 117 can be lowered onto the partitions and/or layer 113F for the actual measurement.

The sensor apparatus 113 or the sensor compartment 118 is fluidically linked to the fluid system 103, in particular to the reaction cavity/cavities 109, preferably by connections, like an inlet 119 and an outlet 120, such that the (treated) sample P, the analytes A or amplification products V can be admitted to the measuring side of the sensor apparatus 113 or sensor array 113A.

The sensor compartment 118 can thus be loaded with fluids and/or said fluids can flow therethrough.

The sensor apparatus 113 preferably comprises a plurality of in particular different capture molecules M, different capture molecules M preferably being arranged and/or immobilized in the (same) sensor compartment 118 and/or in or on different sensor fields 113B and/or preferably being assigned to different sensor fields 113B.

Particularly preferably, the electrodes 113C are provided with capture molecules M, in this case via bonds B, in particular thiol bonds, in particular in order to bond and/or detect or identify suitable analytes A and/or amplification products V.

Different capture molecules M1 to M3 are preferably provided for the different sensor fields 113B and/or the different electrode pairs and/or electrodes 113C, in order to specifically bond different analytes A and/or amplification products V, in FIG. 6 the amplification products V1 to V3, in the sensor fields 113B.

Particularly preferably, the sensor apparatus 113 or sensor array 113A allows the amplification products V bonded in each sensor field 113B to be qualitatively or quantitatively determined.

Preferably, the sensor apparatus 113 comprises capture molecules M having different hybridization temperatures TH, preferably in order to bond the amplification products V to the corresponding capture molecules M at different hybridization temperatures TH.

Preferably, the different capture molecules M having different hybridization temperatures TH are arranged or immobilized in or within the (same) sensor compartment 118 of the sensor apparatus 113. This allows in particular a very compact and simple realization and/or detection or identification of a multiplicity of analytes A, amplification products V and/or groups by means of or within one sensor apparatus 113 or sensor compartment 118.

In order to achieve hybridization at the different hybridization temperatures TH, the temperature of the sensor apparatus 113, in particular of the electrodes 113C, the support 113D, the sensor compartment 118 and/or the sensor cover 117, can be controlled or set, at least indirectly, preferably by means of the analysis device 200, in particular the sensor temperature-control apparatus 204B and/or 204C, as already explained.

Preferably, the sensor temperature-control apparatus 204C is used to temperature-control the sensor compartment 118, in this case by being in contact with the connection side, in particular such that the desired or required hybridization temperature TH is reached on the measuring side, in the sensor compartment 118 and/or in the fluid.

Preferably, in the operating state, the sensor temperature-control apparatus 204C rests on the support 113D in a planar manner and/or centrally and/or so as to be opposite the sensor array 113A and/or rests on one or more contacts 113E at least in part. This makes it possible to particularly rapidly and efficiently temperature-control the sensor compartment 118 and/or amplification products V.

The sensor apparatus 113, in particular the support 113D, preferably comprises at least one, preferably a plurality of, electronic or integrated circuits, the circuits in particular being designed to detect electrical currents or voltages that are preferably generated at the sensor fields 113B in accordance with the redox cycling principle.

Particularly preferably, the measurement signals from the different sensor fields 113E are separately collected or measured by the sensor apparatus 113 and/or the circuits.

Particularly preferably, the sensor apparatus 113 and/or the integrated circuits directly convert the measurement signals into digital signals or data, which can in particular be read out by the analysis device 200.

Particularly preferably, the sensor apparatus 113 and/or the support 113D is constructed as described in EP 1 636 599 B1 and corresponding U.S. Pat. No. 7,914,655.

In the following, a preferred sequence of a test or analysis using the proposed analysis system 1 and/or analysis device 200 and/or the proposed cartridge 100 and/or in accordance with the proposed method is explained in greater detail by way of example.

The analysis system 1, the cartridge 100 and/or the analysis device 200 is preferably designed to carry out the proposed method.

During the proposed method for testing a sample P, at least one analyte A of the sample P is preferably amplified or copied, in particular by means of PCR. The amplified analyte A and/or the amplification products V produced in this way is/are then bonded and/or hybridized to corresponding capture molecules M. The bonded amplification products V are then detected, in particular by means of electronic measurement.

The method may be used in particular in the field of medicine, in particular veterinary medicine, in order to detect diseases and/or pathogens.

Within the context of the method according to the invention, a sample P having at least one analyte A on the basis of a fluid or a liquid from the human or animal body, in particular blood, saliva or urine, is usually first introduced into the receiving cavity 104 via the connection 104A, in order to detect diseases and/or pathogens, it being possible for the sample P to be pretreated.

Once the sample P has been received, the receiving cavity 104 and/or the connection 104A thereof is fluidically closed, in particular in a liquid-tight and/or gas-tight manner.

Preferably, the cartridge 100 together with the sample P is then linked or connected to the analysis device 200, in particular is inserted or slid into the analysis device 200.

The method sequence, in particular the flow and conveying of the fluids, the mixing and the like, is controlled by the analysis device 200 or the control apparatus 207, in particular by accordingly activating and actuating the pump drive 202 or the pump apparatus 112 and/or the actuators 205 or valves 115.

Preferably, the sample P, or some of or a supernatant of the sample P, is removed from the receiving cavity 104 via the outlet 104C and/or the intermediate connection 104D and is fed to the mixing cavity 107 in a metered manner.

Preferably, the sample P in the cartridge 100 is metered, in particular in or by means of the first metering cavity 105A and/or second metering cavity 105B, before being introduced into the mixing cavity 107. Here, in particular the upstream and/or downstream sensor portions 116 are used together with the assigned sensors 206 in order to make possible the desired metering. However, other solutions are also possible.

In the mixing cavity 107, the sample P is prepared for further analysis and/or is mixed with a reagent, preferably with a liquid reagent F1 from a first storage cavity 108A and/or with one or more dry reagents S1, S2 and/or S3, which are preferably provided in the mixing cavity 107.

The liquid and/or dry reagents can be introduced into the mixing cavity 107 before and/or after the sample P. In the example shown, the dry reagents S1 to S3 are preferably introduced into the mixing cavity 107 previously and are optionally dissolved by the sample P and/or the liquid reagent F1.

The liquid reagent F1 may in particular be a reagent, in particular a PCR master mix, for the amplification reaction or PCR. Preferably, the PCR master mix contains nuclease-free water, enzymes for carrying out the PCR, in particular at least one DNA polymerase, nucleoside triphosphates (NTPs), in particular deoxynucleotides (dNTPs), salts, in particular magnesium chloride, and/or reaction buffers.

The dry reagents S1, S2 and/or S3 may likewise be reagents required for carrying out an amplification reaction or PCR, which are in a dry, in particular lyophilised, form. Preferably, the dry reagents S1, S2 and/or S3 are selected in particular from lyophilised enzymes, preferably DNA polymerases, NTPs, dNTPs and/or salts, preferably magnesium chloride.

The dissolving or mixing in the mixing cavity 107 takes place or is assisted in particular by introducing and/or blowing in gas or air, in particular from the bottom. This is carried out in particular by accordingly pumping gas or air in the circuit by means of the pump or pump apparatus 112.

Subsequently, a desired volume of the sample P that is mixed and/or pretreated in the mixing cavity 107 is preferably fed to one or more reaction cavities 109, particularly preferably via (respectively) one of the upstream, optional intermediate cavities 106A to 106C and/or with different reagents or primers, in this case dry reagents S4 to S6, being added or dissolved.

Particularly preferably, the (premixed) sample P is split into several sample portions, preferably of equal size, and/or is divided between the intermediate cavities 106A to 106C and/or reaction cavities 109, preferably evenly and/or in sample portions of equal size.

Different reagents, in the present case dry reagents S4 to S6, particularly preferably primers, in particular those required for the PCR or PCRs, in particular groups of different primers in this case, are preferably added to the (premixed) sample P in the intermediate cavities 106A to 106C and/or different reaction cavities 109, respectively.

The primers in the different groups differ in particular in terms of the hybridization temperatures of the amplification products V produced by the respective primers. As a result, in particular the different group temperatures of the groups of analytes A and/or amplification products V are produced, as already mentioned at the outset.

Particularly preferably, marker primers are used in the sense already specified at the outset.

In the embodiment shown, the reagents or primers S4 to S6 are contained in the intermediate cavities 106A to 106C. However, other solutions are also possible, in particular those in which the reagents or primers S4 to S6 are contained in the reaction cavities 109.

According to a preferred embodiment, the intermediate cavities 106A to 106C each contain primers for amplifying/copying one analyte A, preferably two different analytes A and more preferably three different analytes A. However, it is also possible for four or more different analytes A to be amplified/copied per reaction cavity 109.

Particularly preferably, the reaction cavities 109 are filled in succession with a specified volume of the (pretreated) sample P or with respective sample portions via the intermediate cavities 106A to 106C that are each arranged upstream. For example, the first reaction cavity 109A is filled with a specified volume of the pretreated sample P before the second reaction cavity 109B and/or the second reaction cavity 109E is filled therewith before the third reaction cavity 109C.

In the reaction cavities 109, the amplification reactions or PCRs are carried out to copy/amplify the analytes A. This is carried out in particular by means of the assigned, preferably common, reaction temperature-control apparatus(es) 204A and/or preferably simultaneously for all the reaction cavities 109, i.e. in particular using the same cycles and/or temperature (curves/profiles).

The PCR or PCRs are carried out on the basis of protocols or temperature profiles that are essentially known to a person skilled in the art. In particular, the mixture or sample volume located in the reaction cavities 109 is preferably cyclically heated and cooled.

Preferably, nucleic-acid products are produced from the analytes A as amplification products V in the reaction cavity/cavities 109.

During the pretreatment, reaction and/or PCR or amplification, a label L is directly produced (in each case) and/or is attached to the amplification products V. This is in particular achieved by using corresponding, preferably biotinylated, primers. However, the label L can also be produced and/or bonded to the amplification products V separately or later, optionally also only in the sensor compartment 118 and/or after hybridization.

The label L is used in particular for detecting bonded amplification products V. In particular, the label L can be detected or the label L can be identified in a detection process, as explained in greater detail in the following.

According to the invention, it is possible for a plurality of amplification reactions or PCRs to be carried out in parallel and/or independently from one another using different primers S4 to S6 and/or primer pairs, such that a large number of (different) analytes A can be copied or amplified in parallel and subsequently analyzed.

In particular, identical or different analytes A1 are amplified in the first reaction cavity 109A, identical or different analytes A2 are amplified in the second reaction cavity 109B and identical or different analytes A3 are amplified in the third reaction cavity 109C, preferably by means of amplification reactions, in particular PCRs, that run in parallel.

Particularly preferably, the analytes A1 to A3 are different from one another, in particular such that a large number of different analytes A can be amplified and/or tested by means of the method. Preferably, more than 2 or 4, particularly preferably more than 8 or 11, in particular more than 14 or 17, analytes A can be tested and/or amplified, in particular at the same time.

In particular, a plurality of groups of amplification products V of the analytes A are formed and/or produced, preferably in parallel and/or independently from one another and/or in the reaction cavities 109. Therefore, for example, a first group of amplification products V1 of the analytes A1 is formed and/or produced in the first reaction cavity 109A, a second group of amplification products V2 of the analytes A2 is formed and/or produced in the second reaction cavity 109B, and a third group of amplification products V3 of the analytes A3 is formed and/or produced in the optional third reaction cavity 109C.

Particularly preferably, groups of (amplified) analytes A and/or amplification products V are formed that have different group temperatures in the sense mentioned at the outset. The groups thus preferably have different (optimal) hybridization temperatures TH and/or ranges of hybridization temperatures.

Preferably, different groups of analytes A and/or amplification products V, i.e. in particular nucleic-acid products and/or sequences, are thus amplified and/or formed for the test, it being possible, for the different groups to be amplified and/or formed and/or provided in particular in the different reaction chambers 109A to 109C, but alternatively also in a different manner.

After carrying out the PCR and/or amplification, corresponding fluid volumes and/or amplification products V and/or the groups are conducted out of the reaction cavities 109 in succession to the sensor apparatus 113 and/or to the sensor compartment 118, in particular via a group-specific and/or separate intermediate cavity 106E, 106F or 106G (respectively) and/or via the optional (common) intermediate temperature-control cavity 110.

The intermediate cavities 106E to 106G may contain further reagents, in this case dry reagents S9 and S10, respectively, for preparing the amplification products V for the hybridization, e.g., a buffer, in particular an SSC buffer, and/or salts for further conditioning. On this basis, further conditioning of the amplification products V can be carried out, in particular in order to improve the efficiency of the subsequent hybridization (bonding to the capture molecules M). Particularly preferably, the pH of the sample P is set or optimized in the intermediate cavities 106E to 106G and/or by means of the dry reagents S9 and S10.

Preferably, the sample P or the analytes A and/or amplification products V or groups formed thereby is/axe, in particular immediately before being fed to the sensor apparatus 113 and/or between the reaction cavities 109 and the sensor apparatus 113, actively temperature-controlled (in particular in advance and/or before being temperature-controlled in the sensor apparatus 113), preferably preheated, in particular by means of and/or in the intermediate temperature-control cavity 110 and/or by means of the intermediate temperature-control apparatus 204B.

Preferably, the groups and/or analytes A or amplification products V of the individual reaction cavities 109 are actively temperature-controlled (in particular in advance and/or before being temperature-controlled in the sensor apparatus 113) and/or fed to the intermediate temperature-control cavity 110 in succession. The groups are in particular fed to the sensor apparatus 113 and/or the sensor compartment 118 in succession being temperature-controlled, in particular in advance and/or before being temperature-controlled in the sensor apparatus 113.

Figure 7:
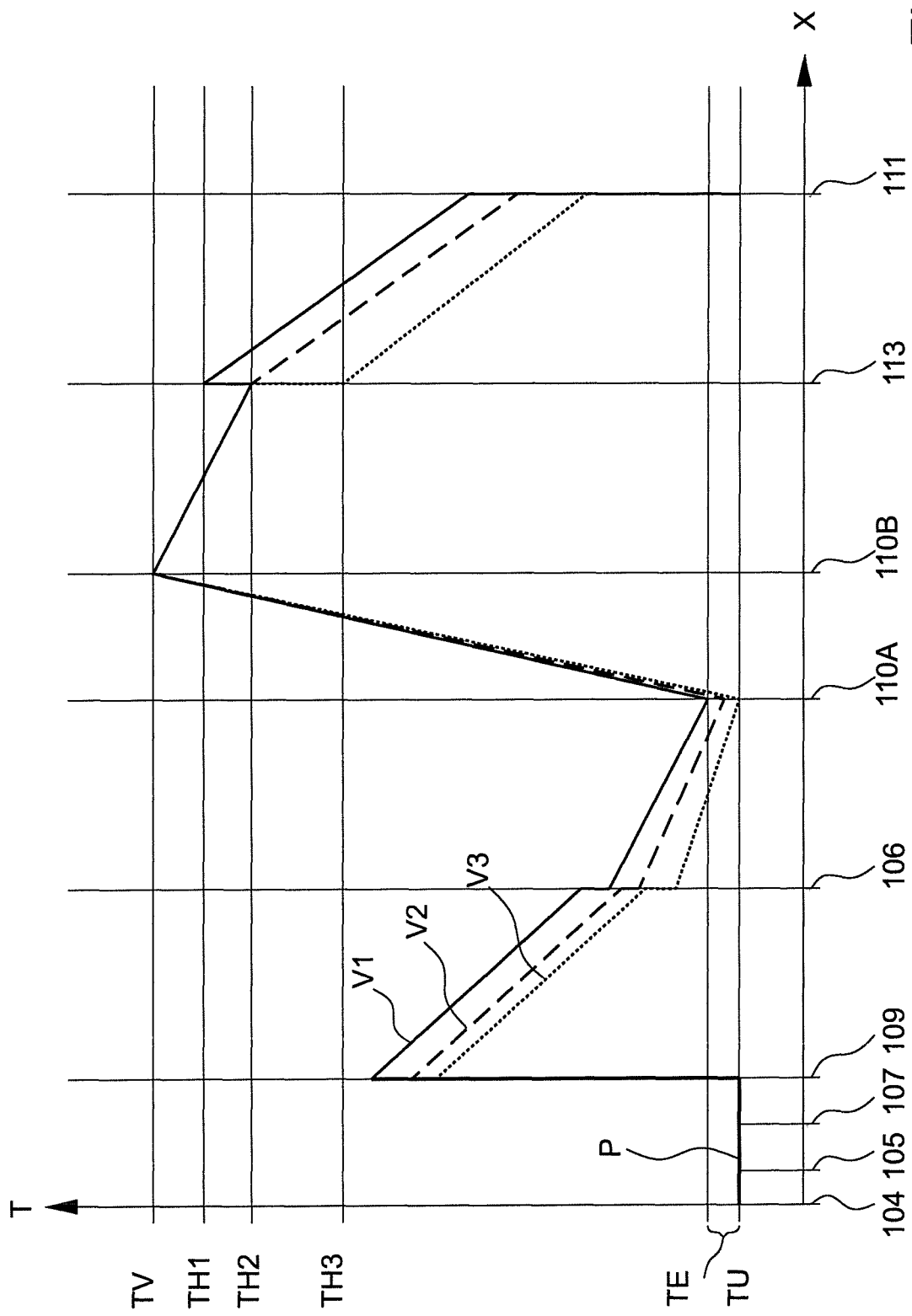
FIG. 7 is a schematic curve or profile for the temperature of the sample and/or of amplification products as a function of the position in the cartridge.

FIG. 7 shows an exemplary schematic curve or profile for the temperature T of the sample P as a function of the position X in or on the cartridge 100.

The sample P is preferably fed to the cartridge 100 and/or receiving cavity 104 at or with an ambient temperature TU, for example of approximately 20° C. The amplification reactions are then carried out in the reaction cavities 109, the prepared sample P preferably being cyclically heated and cooled (not shown in FIG. 7).

As already explained, a plurality of groups having in particular different analytes A and/or amplification products V and/or group temperatures or hybridization temperatures TH are preferably produced.

The groups and/or amplification products V are then preferably fed to the assigned intermediate cavities 106E to 106G and/or to the subsequent intermediate temperature-control cavity 110, preferably in succession.

Preferably, the groups and/or amplification products V cool at different rates and/or continuously in the reaction cavities 109, and/or the groups and/or amplification products V leave the reaction cavities 109 in succession and/or at different temperatures, as shown schematically in FIG. 7. However, other method variants are also possible in which the groups and/or amplification products V are also temperature-controlled and/or kept at a constant temperature in the reaction cavities 109 after the end of the PCRs, preferably such that the groups and/or amplification products V leave the reaction cavities 109 at the same temperature.

Preferably, the groups and/or amplification products V cool on the way to the intermediate temperature-control cavity 110. In this process, the groups and/or amplification products V can cool particularly significantly and/or additionally in the intermediate cavities 106B to 106G by absorbing the reagents S9 and S10 contained in said cavities, as shown in FIG. 7 by a jump in the temperature curve or temperature profile between the reaction cavities 109 and the inlet 110A of the intermediate temperature-control cavity 110, and/or at the reaction cavities 106.

Preferably, the groups and/or amplification products V have different inlet temperatures TE at the inlet 110A of the intermediate temperature-control cavity 110, as shown in FIG. 7 at the inlet 110A, in particular if they have left the reaction cavities 109A to 109C at different temperatures. However, the inlet temperatures TE may also be substantially identical.

The inlet temperature TE at the inlet 110A preferably corresponds at least substantially to the ambient temperature TU or is at most 10° C. or 5° C. above the ambient temperature TU. However, the inlet temperature TE may also be higher if necessary.

Preferably, the groups and/or amplification products V are heated (in succession) in the intermediate temperature-control cavity 110 to a preheat temperature TV and/or melting point or melting temperature, the preheat temperature TV preferably being reached (at the latest) at the outlet 110B of the intermediate temperature-control cavity 110.

Preferably, the preheat temperature TV is higher than the hybridization temperature TH, and in particular at least as high as the melting point or melting temperature of the respective groups and/or amplification products V. In particular, the groups and/or amplification products V are heated to the preheat temperature TV immediately before being fed to the sensor apparatus 113 and/or between the reaction cavities 109 and the sensor apparatus 113, in particular in order to denature the groups and/or amplification products V, as already explained.

As shown in FIG. 7, all the groups and/or amplification products V are preferably heated to the same preheat temperature TV, for example at least 95° C.

However, other method variants are also possible in which the groups and/or amplification products V are temperature-controlled (in particular in advance and/or before being temperature-controlled in the sensor apparatus 113) and/or (pre-)heated to different preheat temperatures TV. In particular, the preheat temperature TV can be varied for each group and/or depending on the required hybridization temperature TH and/or group temperature. In particular, the preheat temperature TV of the first group may be greater than the preheat temperature TV of the second and/or third group and/or the preheat temperature TV may decrease from group to group.

The melting point or melting temperature and/or preheat temperature TV is preferably above the respective hybridization temperatures TH and/or is at least 70° C. or 80° C. and/or at most 99° C. or 96° C., in particular such that bonds of the analytes A and/or amplification products V produced in the meantime dissolve, and/or such that the analytes A and/or amplification products V can be fed to the sensor apparatus 113 in the denatured and/or dissolved state.

Optionally, the analytes A and/or amplification products V and/or the groups of amplification products V are temperature-controlled (in particular in advance and/or before being temperature-controlled in the sensor apparatus 113), in particular (pre-) heated, to the corresponding hybridization temperature TH before being fed to the sensor apparatus 113, preferably such that they can be bonded directly to the corresponding capture molecules M after being fed to the sensor apparatus 113.

In an alternative method variant, the groups and/or amplification products V are actively temperature-controlled, in particular heated, (exclusively) in or on the sensor apparatus 113, and/or brought to the corresponding hybridization temperature TH, preferably solely by means of the sensor temperature-control apparatus 204C. In particular, both the denaturing of any hybridized amplification products V and the (subsequent) hybridization of the amplification products V and the corresponding capture molecules M can take place in or on the sensor apparatus 113. In this case, previous (intermediate) temperature control before the sensor apparatus 113 can therefore be omitted.

In the preferred method variant, the sample P and/or the groups or analytes A and/or amplification products V is/are, however, in particular immediately before being fed to the sensor apparatus 113 and/or between the reaction cavities 109 and the sensor apparatus 113, actively temperature-controlled (in particular in advance and/or before being temperature-controlled in the sensor apparatus 113) and/or brought to the preheat temperature TV, preferably by means of the intermediate temperature-control apparatus 204B, and, after being fed to the sensor apparatus 113 and/or in the sensor apparatus 113, is/are subsequently and/or again temperature-controlled (in particular after being temperature-controlled in the intermediate temperature-control cavity 110) and/or brought to the corresponding hybridization temperature TH and/or group temperature, preferably by means of the sensor temperature-control apparatus 204C. In this case, any hybridized amplification products V are thus denatured before being fed to and/or outside the sensor apparatus 113.

In particular, in the preferred method variant, the sample P and/or the groups and/or amplification products V is/are brought to the respective hybridization temperatures TH and/or group temperatures in multiple stages or more rapidly after leaving the reaction cavity/cavities 109, preferably the amplification products V being, in a first stage, temperature-controlled, in particular in the intermediate temperature-control cavity 110 and/or in advance and/or before being temperature-controlled in the sensor apparatus 113, to a temperature above the hybridization temperature TH and/or to the preheat temperature TV and/or being denatured at the melting point or melting temperature, and, in a second stage, being subsequently and/or again temperature-controlled, in particular heated and/or cooled, to the corresponding hybridization temperature TH and/or group temperature, in particular in the sensor apparatus 113 and/or after being temperature-controlled in the intermediate temperature-control cavity 110.

By means of the sensor temperature-control apparatus 204C, the sensor apparatus 113 is in particular preheated such that in particular undesired cooling of the sample P that is preheated, in this case in the intermediate temperature-control cavity 110, and/or groups, in particular to below the respective hybridization temperatures TH and/or group temperatures, can be prevented.

Particularly preferably, the sensor apparatus 113 is preheated in each case at least substantially to the hybridization temperature TH of the respective analytes A and/or amplification products V, and/or to the respective group temperatures or to a slightly higher or lower temperature. Owing to the relatively large thermal mass of the sensor apparatus 113, the desired and/or optimal temperature for the hybridization can be (rapidly) reached when the preferably warmer sample P and/or group is fed into the sensor apparatus 113 and/or the sensor compartment 118 thereof.

The amplification products V, nucleic-acid products and/or the groups from the reaction cavities 109 are conducted to the sensor apparatus 113 in succession, in particular in order to be detected or determined therein.

Preferably, the first group and/or the amplification products V1 from the first reaction cavity 109A is/are fed to the sensor apparatus 113 and/or bonded to the corresponding capture molecules M1 before the second group and/or the amplification products V2 from the second reaction cavity 109B, in particular the second group and/or the amplification product V2 from the second reaction cavity 109B being bonded to the corresponding capture molecules M2 before the third group and/or the amplification products V3 from the third reaction cavity 109C.

After the sample P and/or the amplification products V are fed to the sensor apparatus 113, the amplification products V are hybridized to the capture molecules M.

In the context of the present invention, it has proven to be particularly advantageous to hybridize the amplification products V and/or groups of the amplification products V at a hybridization temperature TH and/or group temperature that is specifically selected in each case.

Particularly preferably, the sample portions and/or amplification products V from the different PCRs and/or from the different reaction cavities 109 are bonded to the capture molecules M, in particular in succession, at different hybridization temperatures TH and/or at decreasing hybridization temperatures TH and/or group temperatures.

Preferably, the analytes A and/or amplification products V in a group each have a similar, preferably at least substantially identical, (optimal) hybridization temperature TH at which they bond to the suitable capture molecules M. However, it is also possible for the analytes A and/or amplification products V in a group to each have somewhat different (optimal) hybridization temperatures TH, i.e., a range of hybridization temperatures, as already explained at the outset. Therefore, this results in an average and/or optimal hybridization temperature TH of the group or a temperature range of (optimal) hybridization temperatures for this group. This hybridization temperature TH of the group or this temperature range is also referred to as the "group temperature" for short.

The groups and/or amplification products V can be hybridized at a decreasing or increasing, preferably decreasing, group temperature and/or hybridization temperature TH. If a decreasing hybridization temperature TH is used, amplification products V that are already bonded can be prevented from becoming detached from the capture molecules M again due to the subsequent temperature increase.

Particularly preferably, the group temperature and/or hybridization temperature TH1 of the first group, amplification products V1 and/or analytes A1 is greater than the group temperature and/or hybridization temperature TH2 of the second group, amplification products V2 and/or analytes A2, and this temperature is in turn greater than the third group temperature and/or hybridization temperature TH3 of the third group, amplification products V3 and/or analytes A3.

"Hybridization temperature" is understood to mean in particular the temperature at which, on average, the most analytes A and/or amplification products V in the respective groups bond to the suitable capture molecules M.

The group temperatures and/or hybridization temperatures TH of the different groups preferably differ by about 1° C. or more, preferably more than 3° C., in particular more than 4° C., more preferably by approximately 5° C. or more.

Preferably, the group temperature and/or hybridization temperature TH is at least 40° C. or 45° C. and/or at most 75° C. or 70° C.

Preferably, the first group temperature and/or hybridization temperature TH1 of the first group and/or amplification products V1 is at least 55° C. or 58° C., particularly preferably at least 60° C. or 62° C., and/or at most 80° C. or 78° C., particularly preferably at most 75° C. or 72° C.

Preferably, the second group temperature and/or hybridization temperature TH2 of the second group and/or amplification products V2 is at least 40° C. or 45° C., particularly preferably at least 48° C. or 52° C., and/or at most 70° C. or 65° C., particularly preferably at most 60° C. or 58° C.

Preferably, the third group temperature and/or hybridization temperature TH3 of the third group and/or amplification products V3 is at least 35° C. or 40° C., particularly preferably at least 42° C. or 45° C., and/or at most 65° C. or 62° C., particularly preferably at most 60° C. or 55° C.

At the first group temperature and/or hybridization temperature TH1, for example approximately 60° C., the first group bonds particularly well to the corresponding or suitable capture molecules M1. At the second group temperature and/or hybridization temperature TH2, for example approximately 55° C., the second group bonds particularly well to the corresponding or suitable capture molecules M2. At the third group temperature and/or hybridization temperature TH3, for example approximately 50° C., the third group bonds particularly well to the corresponding or suitable capture molecules M3.

As shown in FIG. 7, the groups and/or amplification products V cool on the way from the intermediate temperature-control cavity 110 to the sensor apparatus 113. Depending on the temperature control in advance and/or in the intermediate temperature-control cavity 110, the preheat temperature TV and/or the temperature prevailing when the fluid enters the sensor apparatus 113, and/or depending on the group temperature and/or optimal hybridization temperature TH, it may therefore be necessary to temperature-control individual or all groups and/or amplification products V or the sensor apparatus 113 to different extents by means of the sensor temperature-control apparatus 204C.

For example, the first group and/or the amplification products V1 from the first reaction cavity 109A is/are temperature-controlled, in particular heated, to a greater extent or cooled to a lesser extent than the second group and/or the amplification products V2 from the second reaction cavity 109B and/or the third group and/or amplification products V3 from the third reaction cavity 109C.

In particular, the temperature control of the sensor apparatus 113, in particular of the support 113D, is adapted for each group and/or the different amplification products V in order to reach the respective group temperatures and/or hybridization temperatures TH. For example, the sensor apparatus 113 or the support 113D can be heated (or cooled), preferably by means of the Peltier element or sensor temperature-control apparatus 204C, to different temperatures for the different groups. This heating (or cooling) can be realized by a simple control or feedback-control.

In the example shown, the hybridization temperature TH1 of the first group is above the temperature of the first group at which it enters the sensor apparatus 113, preferably such that the first group and/or the amplification products V1 from the first reaction cavity 109A has/have to be heated for the hybridization, for example by more than 2° C. or 5° C.

The hybridization temperature TH may, however, also correspond to the inlet temperature TE or temperature at entry into the sensor apparatus 113. In this case, the respective groups and/or the amplification products V are kept at a constant temperature in or on the sensor apparatus 113 for the hybridization. In particular, the group and/or the amplification products V may already be fed to the sensor apparatus 113 at the corresponding hybridization temperature TH, as shown in FIG. 7 for the second group and/or the amplification products V2 from the second reaction cavity 109B.

Furthermore, it is possible that the inlet temperature TE or temperature at entry into the sensor apparatus 113 is greater than the hybridization temperature TH of the respective groups and/or of the amplification products V. In this case, the respective groups and/or the amplification products V are cooled or (slightly) temperature-controlled in or on the sensor apparatus 113 for the hybridization such that the temperature is reduced to the required hybridization temperature TH, in particular at a specified speed, as shown in FIG. 7 for the third group and/or the amplification products V3 from the third reaction cavity 109C.

According to the invention, it may be provided both that the hybridization temperature TH is changed in stages, for example in increments of several degrees Celsius and/or in 5° C. increments, and that the hybridization temperature TH is changed, in particular reduced, continuously and/or gradually during the hybridization of a group or at least one analyte A and/or amplification product V.

In another method variant, it may be provided that the respective groups and/or amplification products V in the respective groups are temperature-controlled differently, and/or the temperature is varied in or on the sensor apparatus 113 for the hybridization of the amplification products V in one of the groups, preferably in order to bond the different amplification products V in the respective groups to the corresponding capture molecules M at respectively different hybridization temperatures TH.

Once the sample P, groups, analytes A and/or amplification products V are hybridized and/or bonded to the capture molecules M, detection follows, in particular by means of the preferably provided labels L, or in another manner.

In the following, a particularly preferred variant of the detection is described in greater detail, specifically electrochemical detection, but other types of detection, for example optical detection, capacitive detection or the like, may also be carried out.

Following the respective bonds/hybridizations, preferably an optional washing process takes place and/or additional reagents or liquids, in particular from the storage cavities 108B to 108E, are optionally fed in.

In particular, it may be provided that sample residues and/or unbonded amplification products V, reagents and/or remnants of the PCR and other substances that may disrupt the rest of the method sequence are removed.

Washing or flushing may in particular take place using a fluid and/or reagent F3, in particular a wash buffer, particularly preferably a sodium-citrate buffer or SSC buffer, which is preferably contained in the storage cavity 108C. Unbonded analytes A and/or amplification products V, and substances which could disrupt subsequent detection, are preferably removed from the sensor apparatus 113 and/or fed to the collection cavity 111 by the wash buffer.

Subsequently and/or after the washing process, in accordance with a preferred variant of the method, detection of the amplification products V bonded to the capture molecules M takes place.

In order to detect the amplification products V bonded to the capture molecules M, a reagent F4 and/or detector molecules D, in particular alkaline phosphatase/streptavidin, is/are fed to the sensor apparatus 113, preferably from the storage cavity 108D.

The reagents F4 and/or detector molecules D can bond to the bonded amplification products V, in particular to the label L of the bonded amplification products V, particularly preferably to the biotin marker, as shown in FIG. 6.

In the context of detection, it may also be provided that additional liquid reagents F3 and/or F5 are fed from the storage cavities 108C and/or 108E to the sensor apparatus 113.

Optionally, subsequently or after the reagents F4 and/or detector molecules D have bonded to the amplification products V and/or the labels L, an (additional) washing process and/or flushing takes place, preferably by means of the fluid and/or reagent F3 and/or wash buffer, in particular in order to remove unbonded reagents F4 and/or detector molecules D from the sensor apparatus 113.

Preferably, a reagent S7 and/or S8 and/or substrate SU for the detection, in particular from the storage cavity 106D, is lastly fed to the sensor apparatus 113, preferably together with a fluid or reagent F2 (in particular a buffer), which is suitable for the substrate SU, particularly preferably for dissolving the reagent S7 and/or S8 and/or substrate SU, the fluid or reagent F2 in particular being taken from the storage cavity 108B. In particular, the reagent S7 and/or S8 can form or can comprise the substrate SU.

After adding the substrate SU, the sensor cover 117 is preferably lowered in order to isolate the sensor fields 113B from one another and/or to minimize the exchange of substances therebetween.

Preferably, p-aminophenyl phosphate (pAPP) is used as the substrate SU.

The substrate SU preferably reacts on and/or with the bonded amplification products V and/or detector molecules D and/or allows these to be electrochemically measured.

Preferably, the substrate SU is split by the bonded detector molecules D, in particular the alkaline phosphatase of the bonded detector molecules D, preferably into a first substance SA, such as p-aminophenol, which is in particular electrochemically active and/or redox active, and a second substance SP, such as phosphate.

Preferably, the first or electrochemically active substance SA is detected in the sensor apparatus 113 or in the individual sensor fields 113B by electrochemical measurement and/or redox cycling.

Particularly preferably, by means of the first substance SA, specifically a redox reaction takes place at the electrodes 113C, the first substance SA preferably discharging electrons to or receiving electrons from the electrodes 113C.

In particular, the presence of the first substance SA and/or the respective amounts in the respective sensor fields 113B is detected by the associated redox reactions. In this way, it can be determined qualitatively and in particular also quantitatively whether and how many analytes A and/or amplification products V are bonded to the capture molecules M in the respective sensor fields 113B. This accordingly gives information on which analytes A are or were present in the sample P, and in particular also gives information on the quantity of said analytes A.

In particular, by means of the redox reaction with the first substance SA, an electrical current signal or power signal is generated at the assigned electrodes 113C, the current signal or power signal preferably being detected by means of an assigned electronic circuit.

Depending on the current signal or power signal from the electrodes 113C that is generated in this way, it is determined whether and/or where hybridization to the capture molecules M has occurred.

The measurement is preferably taken just once and/or for the entire sensor array 113A and/or for all the sensor fields 113B, in particular simultaneously or in parallel. In particular, the bonded groups and/or amplification products V from all the groups and/or reaction cavities 109 are detected, identified or determined simultaneously or in parallel in a single or common detection process.

In other words, the amplification products V from the individual reaction cavities 109 that are bonded at different and/or specifically selected hybridization temperatures TH are detected together and/or in parallel, such that rapid measurement is possible, and high specificity in relation to the hybridization of the analytes A and/or amplification products V to the capture molecules M is nevertheless also achieved on the basis of the hybridization temperature TH that is set in a targeted manner in each case.

However, in principle, it is also possible to measure a plurality of sample portions in the sensor apparatus 113 or in a plurality of sensor apparatuses 113 in succession or separately.

The test results or measurement results are in particular electrically transmitted to the analysis device 200 or the control apparatus 207 thereof, preferably by means of the electrical connection apparatus 203, and are accordingly prepared, analyzed, stored, displayed and/or output, in particular by the display apparatus 209 and/or interface 210.

After the test has been carried out, the cartridge 100 is disconnected from the analysis device 200 and/or is released or ejected therefrom, and is in particular disposed of.

Individual aspects and features of the present invention and individual method steps and/or method variants may be implemented independently from one another, but also in any desired combination and/or order.

In particular, the present invention relates also to any one of the following aspects which can be realized independently or in any combination, also in combination with any aspects described above.

1. Method for testing an in particular biological sample (P), wherein amplification products (V) are formed from analytes (A) of the sample (P),
wherein the amplification products (V) are bonded to corresponding capture molecules (M) of a sensor apparatus (113) and the bonded amplification products (V) are detected in a detection process,
characterised in that a first group of amplification products (V1) of at least one first analyte (A1) and a second group of amplification products (V2) of at least one second analyte (A2) are bonded to the corresponding capture molecules (M) at different hybridisation temperatures (TH).

2. Method according to aspect 1, characterised in that the amplification products (V1) of the first group are different from the amplification products (V2) of the second group.

3. Method according to aspect 1 or 2, characterised in that different analytes (A) are amplified in parallel, independently from one another and/or in different reaction cavities (109), and/or the first group and the second group are formed in parallel, independently from one another and/or in different reaction cavities (109), in particular in order to detect the nucleic-acid products and/or amplification products (V) in a detection process.

4. Method according to any one of the preceding aspects, characterised in that the analytes (A) are amplified by means of an amplification reaction, in particular PCR, and/or nucleic-acid products are produced as amplification products (V) from the analytes (A).

5. Method according to any one of the preceding aspects, characterised in that the first group and the second group are fed to the sensor apparatus (113) and/or bonded to the corresponding capture molecules (M) in succession.

6. Method according to any one of the preceding aspects, characterised in that the hybridisation temperature (TH) of the first group is greater than the hybridisation temperature (TH) of the second group, the first group preferably being fed to the sensor apparatus (113) and/or bonded to the corresponding capture molecules (M) before the second group.

7. Method according to any one of the preceding aspects, characterised in that the groups each comprise amplification products (V) of different analytes (A), the different amplification products (V) of the first group and/or second group preferably being bonded to the corresponding capture molecules (M) at respective common hybridisation temperatures (TH) or at respective different hybridisation temperatures (TH).

8. Method according to any one of the preceding aspects, characterised in that the first group and/or the second group is/are bonded to the suitable capture molecules (M) at hybridisation temperatures (TH) of at least 40° C. or 50° C., in particular at least 55° C. or 60° C., and/or at most 75° C. or 70° C., in particular at most 65° C. or 60° C.

9. Method according to any one of the preceding aspects, characterised in that the groups and/or amplification products (V) are detected or determined in a single or common detection process.

10. Method according to any one of the preceding aspects, characterised in that the groups and/or amplification products (V) are actively temperature-controlled, preferably preheated, before the sensor apparatus (113) and/or the hybridisation, in particular again or when the fluid is flowing through, in particular to a temperature above the hybridisation temperature (TH) and/or to at least 70° C. or 80° C. and/or at most 99° C. or 95° C.

11. Method according to any one of the preceding aspects, characterised in that the sensor apparatus (113) and/or the groups and/or amplification products (V) is/are actively temperature-controlled, in particular heated and/or cooled, to the hybridisation temperature (TH) in or on the sensor apparatus (113).

12. Analysis system (1) for testing an in particular biological sample (P),
the analysis system (1) comprising a sensor apparatus (113) having capture molecules (M) for bonding analytes (A) of the sample (P) and/or amplification products (V) of the analytes (A) in order to detect said analytes and/or amplification products in a detection process, characterised
in that the capture molecules (M) have different hybridisation temperatures (TH) in order to bond the analytes (A) and/or amplification products (V) to the corresponding capture molecules (M) at the different hybridisation temperatures (TH), and/or
in that the analysis system (1) is designed to carry out the method according to any one of the preceding aspects.

13. Analysis system according to aspect 12, characterised in that the sensor apparatus (113) comprises a plurality of sensor fields (113B), different capture molecules (M) for bonding and/or detecting different analytes (A) and/or amplification products (V) being arranged in different sensor fields (113B) and/or in that the capture molecules (M) are designed as oligonucleotide probes, in particular having a length of at least 10 or 20 nucleotides and/or at most 40 or 30 nucleotides.

14. Analysis system according to aspect 12 or 13, characterised in that the analysis system (1) comprises a reaction cavity (109) for producing the amplification products (V) or a plurality of reaction cavities (109) for producing different amplification products (V) in parallel and/or independently.

15. Analysis system according to any one of aspects 12 to 14, characterised in that the analysis system (1) comprises a cartridge (100) for receiving the sample (P) and an analysis device (200) for receiving the cartridge (100), preferably the cartridge (100) comprising the sensor apparatus (113) and/or reaction cavity/cavities (109), and/or the analysis device (200) comprising a sensor temperature-control apparatus (204C) for temperature-controlling the sensor apparatus (113) and/or an intermediate temperature-control apparatus (204B) for temperature-controlling the amplification products (V) before the sensor apparatus (113).

What is claimed is:
1. A method for testing a biological sample, comprising:
forming amplification products from analytes of the biological sample in a reaction cavity,
feeding the amplification products from the reaction cavity to a sensor apparatus having a sensor compartment,
bonding the amplification products to corresponding capture molecules of said sensor apparatus and detecting or identifying the bonded amplification products, bonding a first group of amplification products of at least one first analyte and a second group of amplification products of at least one second analyte in the sensor compartment to the corresponding capture molecules at different hybridization temperatures, and performing said feeding of the first group and the second group to the sensor compartment in succession and performing said bonding of the first group and the second group to the corresponding capture molecules in succession at said different hybridization temperatures.

2. The method according to claim 1, wherein the amplification products of the first group are different from the amplification products of the second group.

3. The method according to claim 1, wherein different analytes are amplified in parallel, independently from one another and/or in different reaction cavities.

4. The method according to claim 3, wherein at least one of different analytes and the first group and second group are at least one of amplified and formed in order to detect or identify at least one of nucleic-acid products and amplification products.

5. The method according to claim 1, wherein the first group and the second group are formed in parallel, at least one of independently from one another and in different reaction cavities.

6. The method according to claim 1, wherein the analytes are amplified by means of an amplification reaction.

7. The method according to claim 1, wherein nucleic-acid products are produced as amplification products from the analytes.

8. The method according to claim 1, wherein the sensor apparatus or a sensor array or support thereof is heated to different temperatures for the different groups.

9. The method according to claim 1, wherein the groups are successively hybridized with decreasing hybridization temperature.

10. The method according to claim 1, wherein the hybridization temperature of the first group is greater than the hybridization temperature of the second group.

11. The method according to claim 10, wherein the first group is at least one of fed to the sensor apparatus and bonded to corresponding capture molecules before the second group.

12. The method according to claim 1, wherein the hybridization temperatures of the different groups differ by at least 1° C.

13. The method according to claim 1, wherein the groups each comprise amplification products of different analytes.

14. The method according to claim 13, wherein the different amplification products of the first group and second group, respectively, are bonded to the corresponding capture molecules at a common hybridization temperature, respectively.

15. The method according to claim 13, wherein the common hybridization temperatures of the different groups are different by at least 1° C.

16. The method according to claim 1, wherein the groups and/or amplification products are detected, identified or determined in a single or common detection process.

17. The method according to claim 1, wherein at least one the groups and amplification products are actively temperature-controlled or preheated before at least one the sensor apparatus and hybridization.

18. The method according to claim 1, wherein at least one the groups and amplification products are preheated to a temperature above the hybridization temperature before being fed to the sensor compartment.

19. The method according to claim 1, wherein at least one the groups and amplification products are preheated to at least 70° C. before being fed to the sensor compartment.

20. The method according to claim 1, wherein at least one of the sensor apparatus, the groups and the amplification products is actively temperature-controlled to the hybridization temperature in or on the sensor apparatus.

21. The method according to claim 1, wherein the first group is heated, to a greater extent or cooled to a lesser extent than the second group.

22. The method according to claim 1, wherein a temperature control of the sensor apparatus is adapted differently for each group in order to reach the respective hybridization temperatures.

* * * * *